US008485975B2

(12) United States Patent
Suri

(10) Patent No.: US 8,485,975 B2
(45) Date of Patent: *Jul. 16, 2013

(54) MULTI-RESOLUTION EDGE FLOW APPROACH TO VASCULAR ULTRASOUND FOR INTIMA-MEDIA THICKNESS (IMT) MEASUREMENT

(75) Inventor: Jasjit S. Suri, Roseville, CA (US)

(73) Assignee: AtheroPoint LLC, Roseville, CA (US)

( * ) Notice: Subject to any disclaimer, the term of this patent is extended or adjusted under 35 U.S.C. 154(b) by 256 days.

This patent is subject to a terminal disclaimer.

(21) Appl. No.: 12/896,875

(22) Filed: Oct. 2, 2010

(65) Prior Publication Data

US 2011/0299753 A1    Dec. 8, 2011

Related U.S. Application Data

(63) Continuation-in-part of application No. 12/802,431, filed on Jun. 7, 2010, now Pat. No. 8,313,437.

(51) Int. Cl.
*A61B 8/00* (2006.01)
*G06K 9/00* (2006.01)

(52) U.S. Cl.
USPC ............ 600/443; 600/437; 600/465; 382/128

(58) Field of Classification Search
USPC ........................... 600/437, 443, 465; 382/128
See application file for complete search history.

(56) References Cited

U.S. PATENT DOCUMENTS

| 5,343,867 A | 9/1994 | Shankar |
| 5,734,739 A | 3/1998 | Sheehan et al. |
| 6,132,373 A | 10/2000 | Ito et al. |
| 6,251,072 B1 | 6/2001 | Ladak et al. |
| 6,267,728 B1 | 7/2001 | Hayden |
| 6,347,152 B1 | 2/2002 | Shinagawa et al. |
| 6,597,937 B2 | 7/2003 | Liu et al. |

(Continued)

FOREIGN PATENT DOCUMENTS

WO    WO03042921 A    5/2003

OTHER PUBLICATIONS

Gutierrez, Marco et al. "Assessment of carotid diameter and wall thickness in ultrasound images using active contours improved by a multiresolution technique". Medical Imaging 2002: Physiology and Function from Multidimensional Images, Proceedings of SPIE vol. 4683.*

*Primary Examiner* — Michael Rozanski
*Assistant Examiner* — Helene Bor
(74) *Attorney, Agent, or Firm* — Inventive Patent Law P.C.; Jim H. Salter

(57) ABSTRACT

A computer-implemented system and method for fast, reliable, and automated embodiments for using a multi-resolution edge flow approach to vascular ultrasound for intima-media thickness (IMT) measurement. Various embodiments include receiving biomedical imaging data and patient demographic data corresponding to a current scan of a patient; checking the biomedical imaging data in real-time to determine if an artery of the patient has a calcium deposit in a proximal wall of the artery; acquiring arterial data of the patient as a combination of longitudinal B-mode and transverse B-mode data; using a data processor to automatically recognize the artery; using the data processor to calibrate a region of interest around the automatically recognized artery; automatically computing the weak or missing edges of intima-media and media-adventitia walls using edge flow, labeling and connectivity; and determining the intima-media thickness (IMT) of an arterial wall of the automatically recognized artery.

17 Claims, 39 Drawing Sheets

U.S. PATENT DOCUMENTS

| | | |
|---|---|---|
| 6,614,453 B1 | 9/2003 | Suri et al. |
| 6,718,055 B1 | 4/2004 | Suri |
| 6,785,409 B1 | 8/2004 | Suri |
| 6,813,373 B1 | 11/2004 | Suri et al. |
| 6,817,982 B2 | 11/2004 | Fritz et al. |
| 6,835,177 B2 | 12/2004 | Fritz et al. |
| 6,842,638 B1 | 1/2005 | Suri et al. |
| 6,845,260 B2 | 1/2005 | Liu et al. |
| 6,987,568 B2 | 1/2006 | Dana |
| 7,020,314 B1 | 3/2006 | Suri et al. |
| 7,024,027 B1 | 4/2006 | Suri et al. |
| 7,074,187 B2 | 7/2006 | Selzer et al. |
| 7,090,640 B2 * | 8/2006 | Barth et al. .................. 600/443 |
| 7,110,000 B2 | 9/2006 | Zhang et al. |
| 7,149,368 B2 | 12/2006 | Tong et al. |
| 7,161,601 B2 | 1/2007 | Zhang et al. |
| 7,272,241 B2 | 9/2007 | Demi et al. |
| 7,340,083 B2 | 3/2008 | Yuan et al. |
| 7,353,117 B2 | 4/2008 | Yuan et al. |
| 7,376,253 B2 | 5/2008 | Spreeuwers et al. |
| 7,639,261 B2 | 12/2009 | Sekine et al. |
| 7,657,299 B2 | 2/2010 | Huizenga et al. |
| 7,680,330 B2 | 3/2010 | Leung |
| 7,686,764 B2 * | 3/2010 | Watanabe et al. ............. 600/443 |
| 2003/0053669 A1 | 3/2003 | Suri et al. |
| 2003/0236460 A1 | 12/2003 | Ma et al. |
| 2004/0116808 A1 * | 6/2004 | Fritz et al. .................... 600/437 |
| 2004/0243365 A1 | 12/2004 | Yuan et al. |
| 2005/0042222 A1 | 2/2005 | Yamamoto et al. |
| 2005/0043614 A1 | 2/2005 | Huizenga et al. |
| 2005/0119555 A1 | 6/2005 | Fritz et al. |
| 2005/0267365 A1 * | 12/2005 | Sokulin et al. ................ 600/437 |
| 2006/0064016 A1 | 3/2006 | Demi et al. |
| 2006/0241465 A1 | 10/2006 | Huennekens et al. |
| 2007/0003116 A1 | 1/2007 | Yuan et al. |
| 2007/0038061 A1 | 2/2007 | Huennekens et al. |
| 2007/0269086 A1 | 11/2007 | Kerwin et al. |
| 2007/0287897 A1 | 12/2007 | Faris |
| 2008/0009702 A1 | 1/2008 | Liu et al. |
| 2008/0051658 A1 | 2/2008 | Demi et al. |
| 2008/0080755 A1 | 4/2008 | Payonk et al. |
| 2008/0095422 A1 | 4/2008 | Suri et al. |
| 2008/0145841 A1 | 6/2008 | Libutti et al. |
| 2008/0171939 A1 | 7/2008 | Ishihara |
| 2008/0221446 A1 | 9/2008 | Washburn et al. |
| 2008/0269595 A1 | 10/2008 | Wong |
| 2008/0274457 A1 | 11/2008 | Eng et al. |
| 2008/0316374 A1 | 12/2008 | Koike et al. |
| 2009/0028793 A1 | 1/2009 | Neri et al. |
| 2009/0252395 A1 | 10/2009 | Chan et al. |
| 2010/0060644 A1 | 3/2010 | Elie et al. |
| 2010/0081931 A1 | 4/2010 | Destrempes et al. |

\* cited by examiner

FIGURE 16 (Cropped Images with different geometries)

FIGURE 17 (Despeckle Filtering)

FIGURE 18 (Down Sampled Images)

FIGURE 19 (Recognition Phase of Far Adventitia)

FIGURE 20 (Guidance Zone)

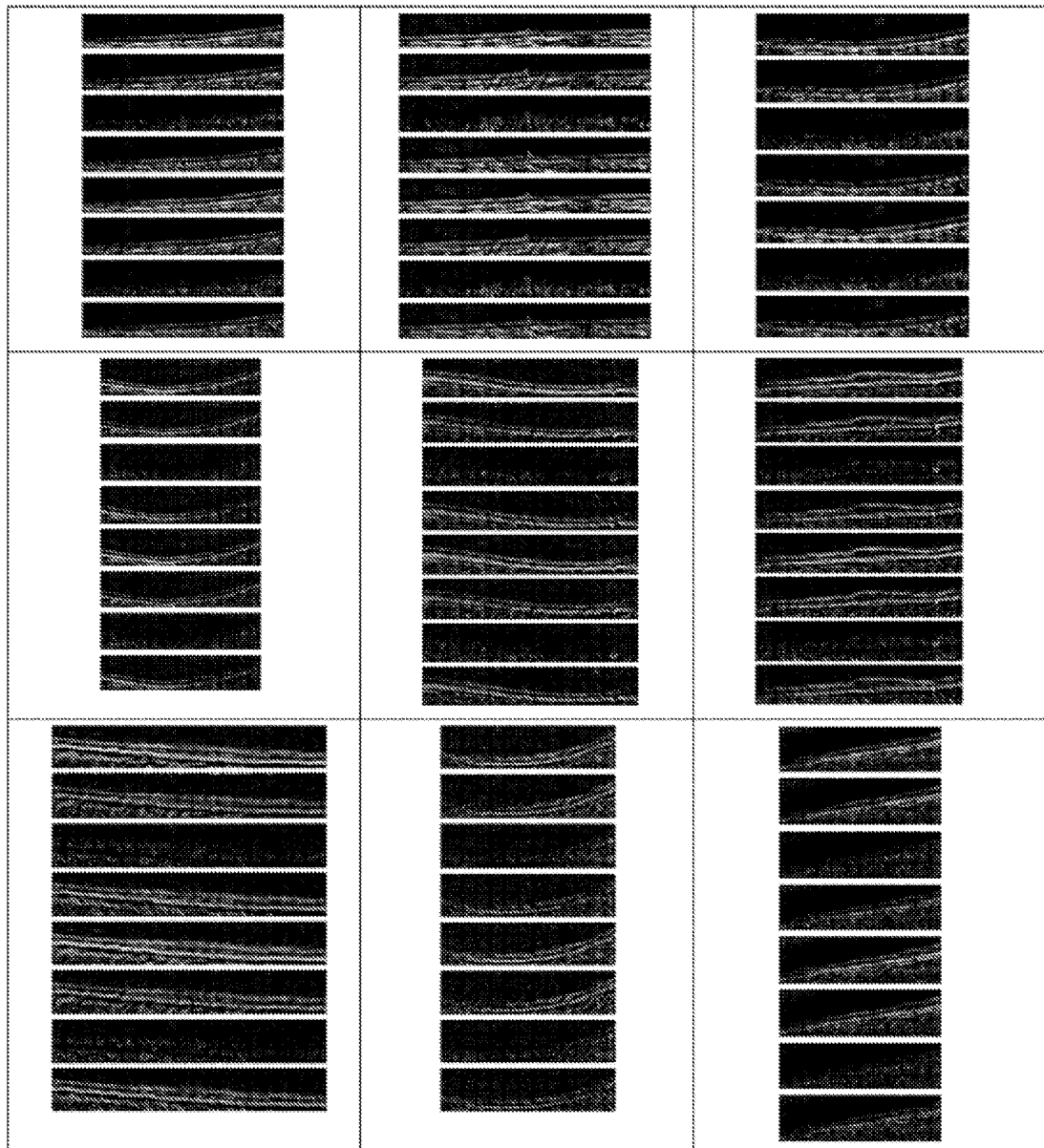
FIGURE 22A (Edge Flow Energy at different angles)

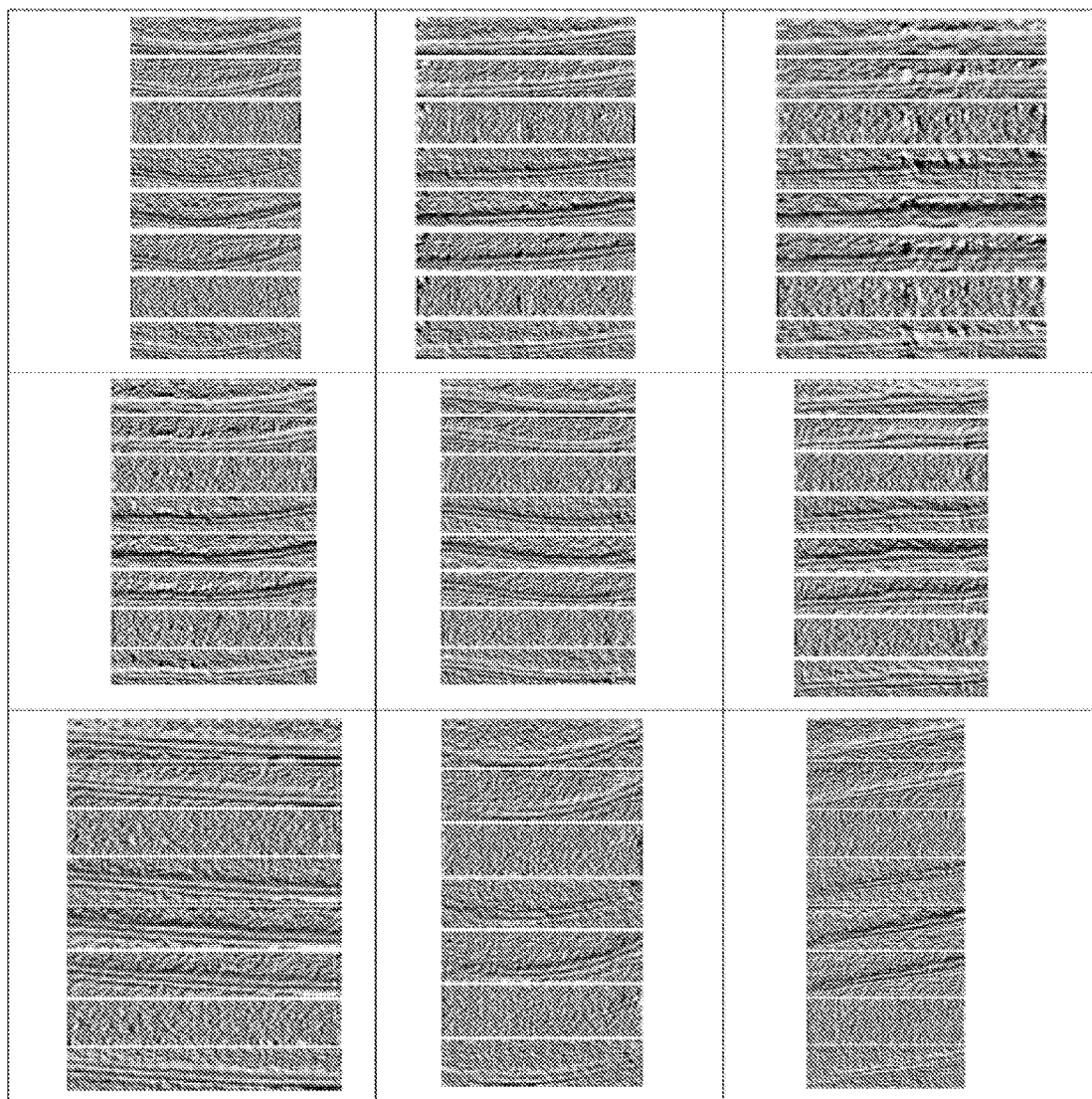
FIGURE 22B (Probability Maps)

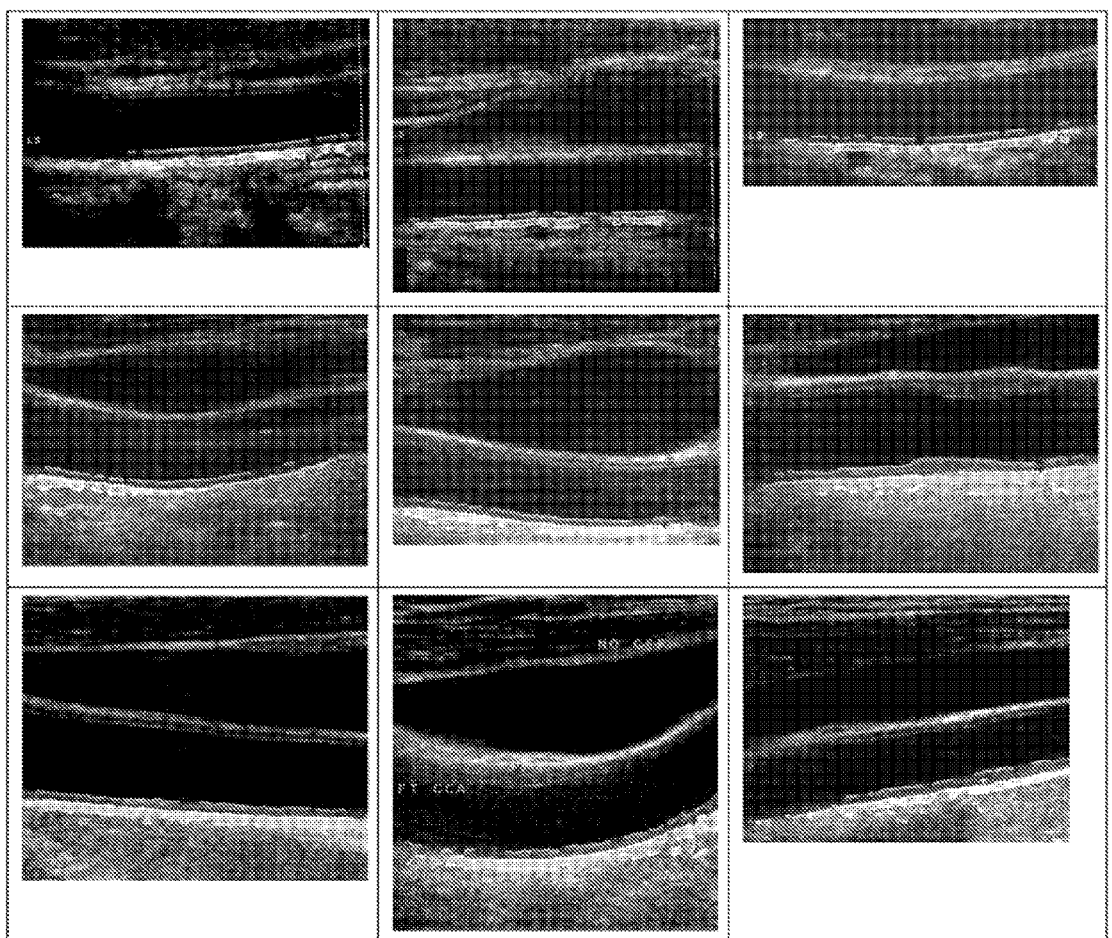
FIGURE 23 (Strong Edges of MA and LI)

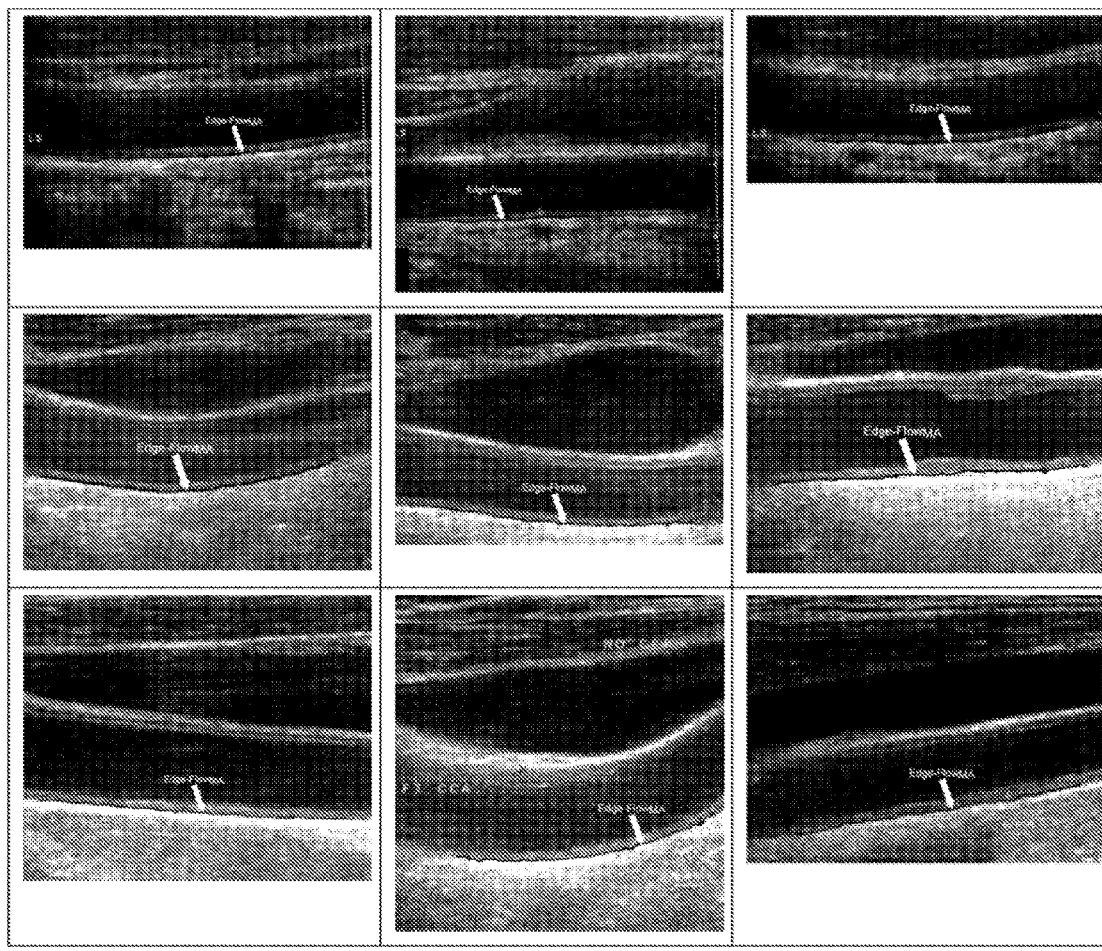
FIGURE 24B (MA Refinement using Edge Flow Method)

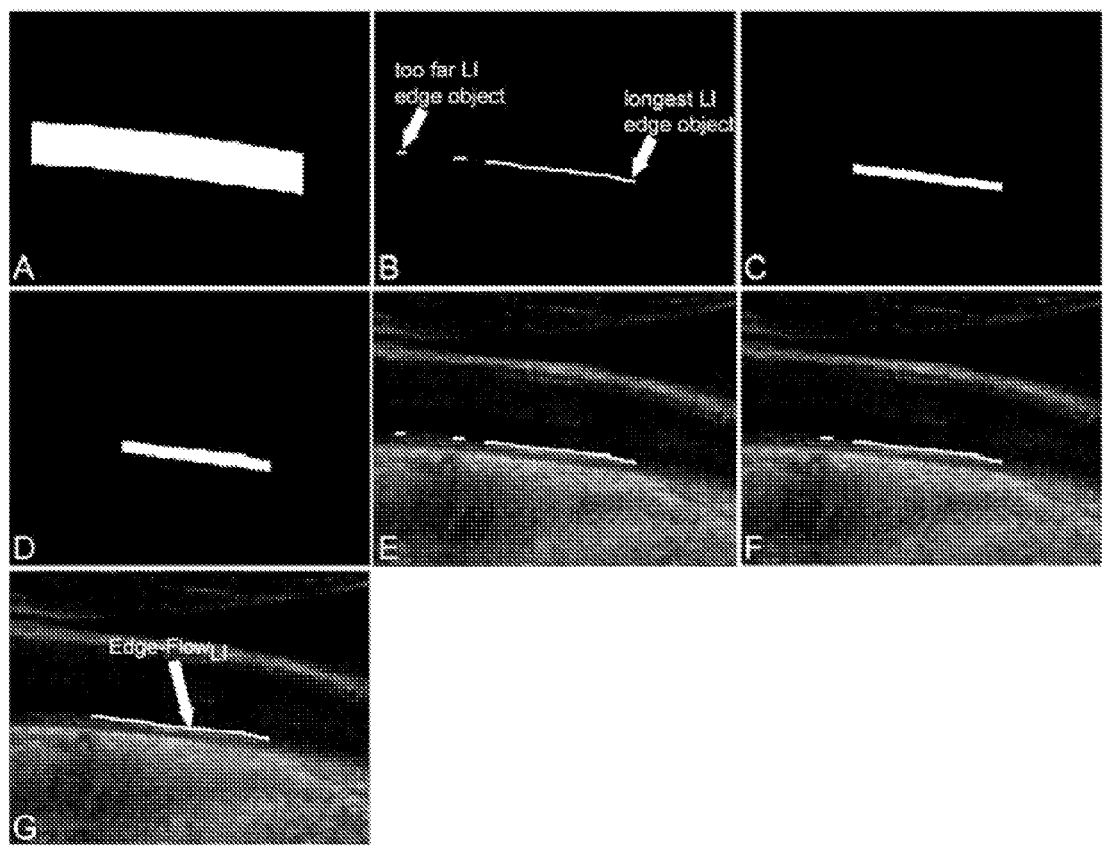
FIGURE 25 (LI Estimation from MA)

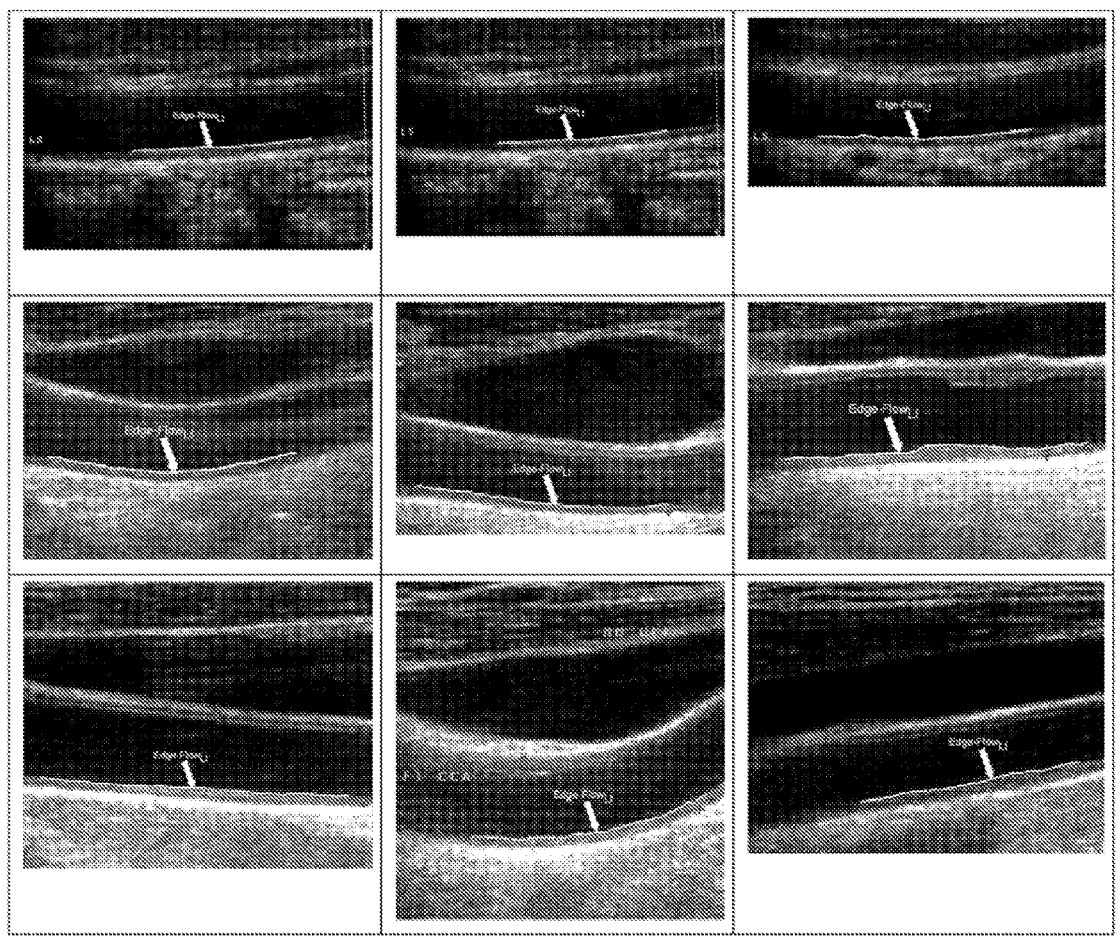
FIGURE 26 (LI Refinement – Edge Flow Process)

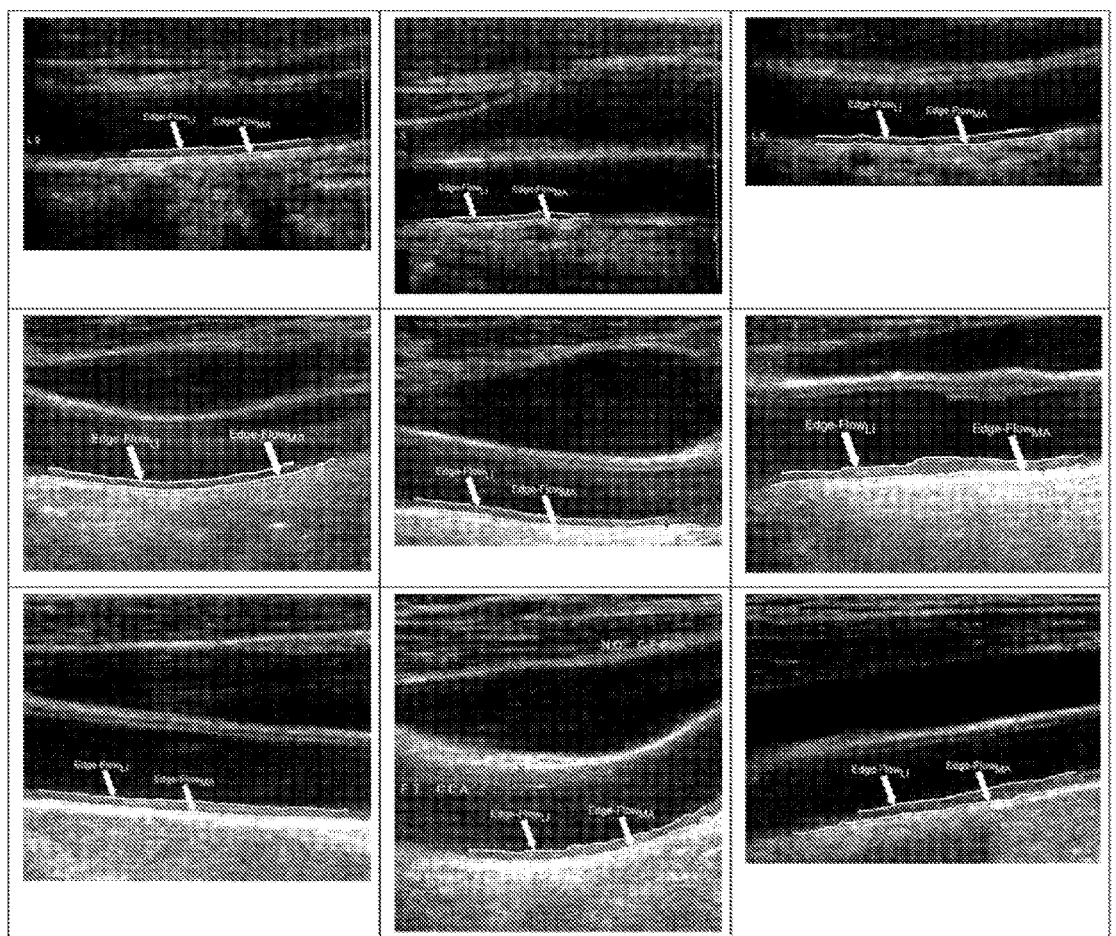
FIGURE 27 (LI and MA Borders using Edge Flow)

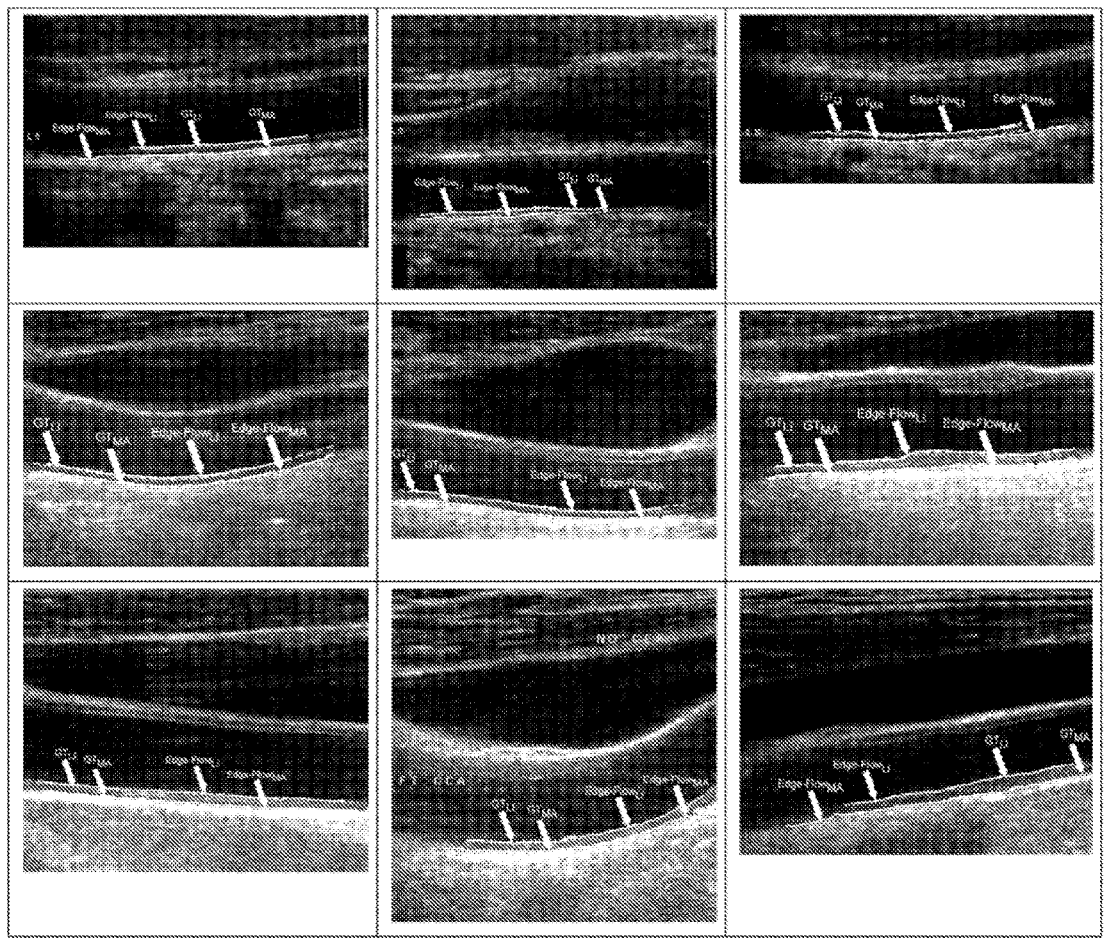
FIGURE 28B (LIMA Borders using EDGE FLOW Method Vs. GT)

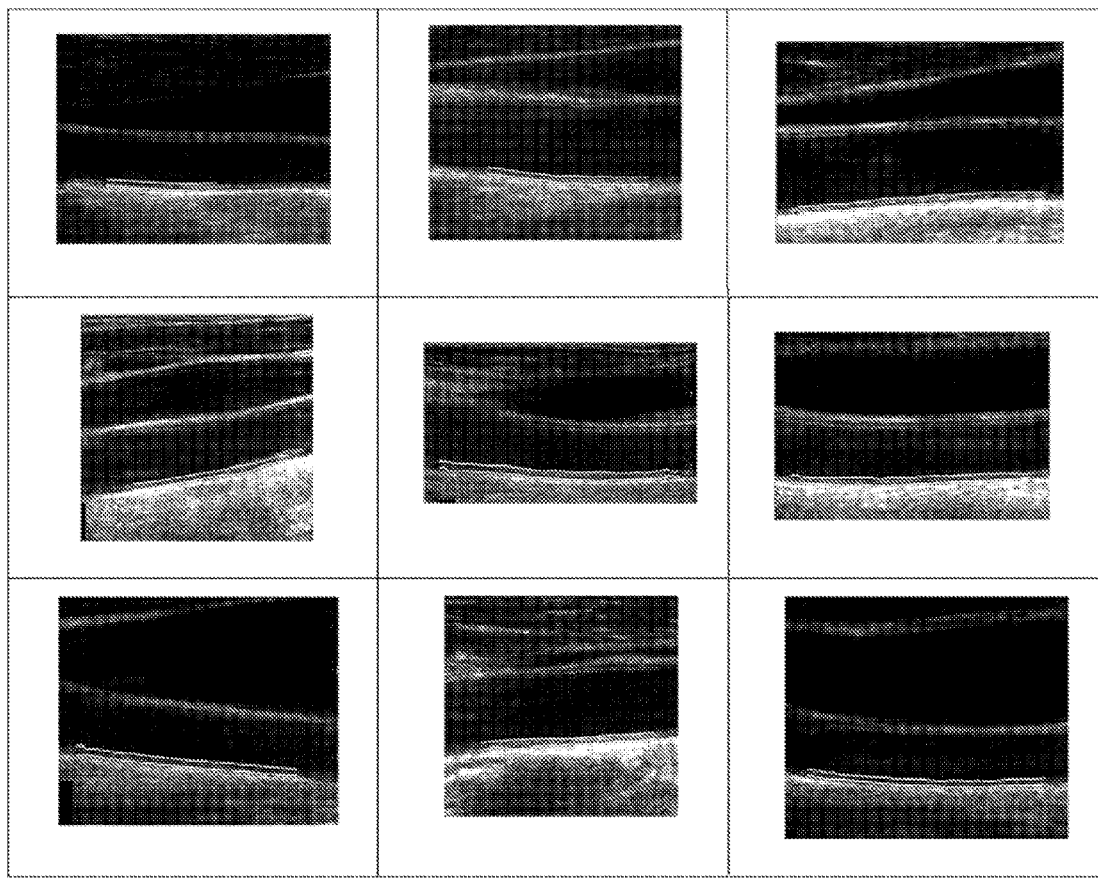
FIGURE 29A (LIMA Borders, EDGE FLOW METHOD)

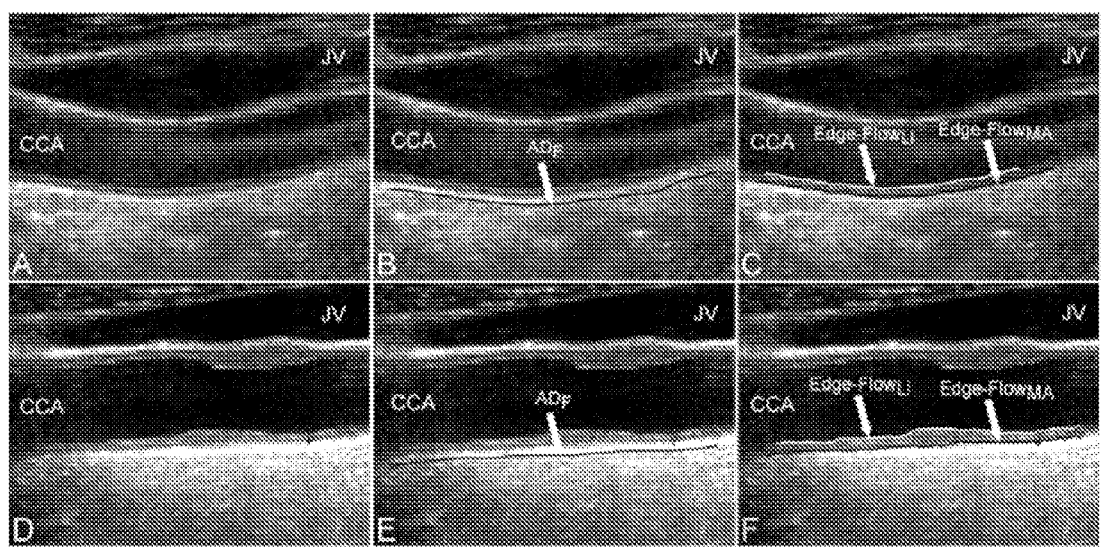
FIGURE 29B (LIMA Borders, EDGE FLOW METHOD)

FIGURE 31 Processing using MOMENTS

FIGURE 32 (stage II, CAMES)

MULTI-RESOLUTION EDGE FLOW APPROACH TO VASCULAR ULTRASOUND FOR INTIMA-MEDIA THICKNESS (IMT) MEASUREMENT

PRIORITY APPLICATION

This is a continuation-in-part patent application of patent application Ser. No. 12/802,431; filed Jun. 7, 2010 now U.S. Pat. No. 8,313,437 by the same applicant. This present patent application draws priority from the referenced co-pending patent application. The entire disclosure of the referenced co-pending patent application is considered part of the disclosure of the present application and is hereby incorporated by reference herein in its entirety.

COPYRIGHT

A portion of the disclosure of this patent document contains material that is subject to copyright protection. The copyright owner has no objection to the facsimile reproduction of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2009-2010 Jasjit S. Sari, Biomedical Technologies Inc., All Rights Reserved.

TECHNICAL FIELD

This patent application relates to methods and systems for use with data processing, data storage, and imaging systems, according to one embodiment, and more specifically, for ultrasound image processing.

BACKGROUND

The state of Atherosclerosis in carotids or other blood vessels can be studied using Magnetic Resonance Imaging (MRI) or Ultrasound. Because ultrasound offers several advantages like real time scanning of carotids, compact in size, low cost, easy to transport (portability), easy availability and visualization of the arteries are possible, Atherosclerosis quantification is taking a new dimension using ultrasound. Because one can achieve compound and harmonic imaging which generates high quality images with ultrasound, it is thus possible to do two-dimensional (2D) and three-dimensional (3D) imaging of carotid ultrasound for monitoring of Atherosclerosis.

In recent years, the possibility of adopting a composite thickness of the tunica intima and media, i.e., an intima-media thickness (hereinafter referred to as an "IMT") of carotid arteries, as surrogate market for cardiovascular risk and stroke. Conventional methods of imaging a carotid artery using an ultrasound system, and measuring the IMT using an ultrasonic image for the purpose of diagnosis are being developed.

A conventional measuring apparatus can measure an intima-media thickness of a blood vessel using an ultrasound device to scan the blood vessel. Then, for example, an image of a section of the blood vessel including sections of the intima, media and adventitia is obtained. The ultrasound device further produces digital image data representing this image, and outputs the digital image data to a data analyzing device.

The intima, media and adventitia can be discriminated on the basis of changes in density of tissue thereof. A change in density of tissue of the blood vessel appears as a change of luminance values in the digital image data. The data analyzing device detects and calculates the intima-media thickness on the basis of the changes of luminance values in the digital image data. The digital image data can include a plurality of luminance values each corresponding to respective one of a plurality of pixels of the image. The data analyzing device can set a base position between a center of the blood vessel and a position in a vicinity of an inner intimal wall of the blood vessel on the image, on the basis of a moving average of the luminance values. The data analyzing device can detect a maximum value and a minimum value from among the luminance values respectively corresponding to a predetermined number of the pixels arranged from the base position toward a position of an outer adventitial wall on the image. The data analyzing device can then calculate the intima-media thickness on the basis of the maximum value and the minimum value.

The major challenges which can be affected in finding the IMT are: (a) how well the ultrasound probe is gripped with the neck of a patient to scan the carotids; (b) how well the ultrasound gel is being applied; (c) the orientation of the probe; (d) demographics of the patient; (e) skills of the sonographer or vascular surgeon; and (f) threshold chosen for finding the peaks corresponding to the lumen-intima (LI) border points, and the media-adventitia (MA) border points (collectively denoted herein as the LIMA or LIMA points) for each signal orthogonal to the lumen.

Thus, a system and method for fast, reliable, and automated embodiments for using a multi-resolution edge flow approach to vascular ultrasound for intima-media thickness (IMT) measurement is needed.

BRIEF DESCRIPTION OF THE DRAWINGS

FIG. 3 shows that if there is a calcium cone shadow computes the IMT by correcting the IMT so-called the shadow correction. Shadow corrected processes estimate the IMT values under calcium shadow projection, while these processes simply run if there is no calcium shadow cone.

FIG. 21 shows an example of the total Edge Flow computed in eight orientations. (A) Total Edge Flow energy. (B) Total Edge Flow probability. On top of the columns, the grayscale Guidance Zone is shown.

FIGS. 22A and 22B show the edge flow intensity and probability.

FIGS. 23, 24A, and 24B show the MA refinement edges. In FIG. 24A, steps show the refinement of weak. MA or missing MA edges: (A) Results of the Edge Flow segmentation showing edge objects located below the $AD_F$, isolated small edge object, and chunk. (B) Removal of edge objects that are below the $AD_F$ and isolated edge object. (C) Edge objects that are classified as being part of the MA segment overlaid on the original grayscale (D) Final MA profile on the original image.

FIG. 25 shows the step-by-step methodology for LI estimation.

FIG. 26 shows the LI refinement edges.

FIG. 27 shows the LIMA edges.

FIGS. 28A and 28B show the LI results with Ground Truth (GT) in comparison. FIG. 28A shows a comparison between Edge Flow and expert tracings (GT) of the LI and MA borders. The Edge Flow tracings are depicted by continuous solid lines, whereas dotted lines indicate the GT tracings. Left Image: non-horizontal geometry: Right Image: carotid artery in the presence of jugular vein.

FIGS. 29A and 29B show the LIMA borders. FIG. 29B shows examples of Edge Flow performance on a normal but non-horizontal carotid artery and a carotid artery in the presence of a jugular vein. First Column: the original cropped images; Middle Column: $AD_F$ profile (stage-I output) overlaid on the original cropped grayscale images; Last Column: LI and MA borders estimated using the Edge Flow process described herein as overlaid on the original grayscale images. Top Row: Normal CA that is not horizontal and that is corrupted by blood backscattering. Bottom Row: Vessel with a thicker artery wall and in the presence of the jugular vein in the image (CCA—common carotid artery; JV—jugular vein).

FIG. 30 shows a Distribution of $\epsilon_{ADF-GT}^{LI}$ and $\epsilon_{ADF-GT}^{MA}$ for Edge Flow, CALEXia and CULEXsa. (A) and (B): LI and MA errors for Edge Flow, respectively. (C) and (D): LI and MA errors for CALEXia, respectively. (E) and (F): LI and MA errors for CULEXsa, respectively. The horizontal axis represents the error classes in millimeters and the vertical axis represents the cumulative frequency. The black lines represent the cumulative function of the error distributions.

DETAILED DESCRIPTION

Figure 1A:
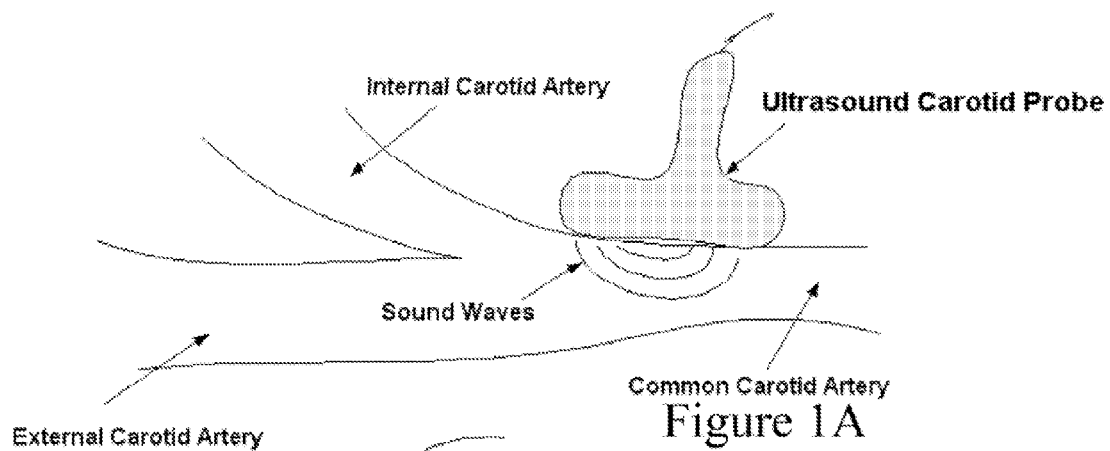
FIG. 1A shows the ultrasound scanning of the Carotid Artery. This can be a common carotid artery (CCA) or an internal carotid artery (ICA).

In the following description, for purposes of explanation, numerous specific details are set forth in order to provide a thorough understanding of the various embodiments. It will be evident, however, to one of ordinary skill in the art that the various embodiments may be practiced without these specific details.

This patent application discloses various embodiments of a computer-implemented system and method for fast, reliable, and automated embodiments for using a multi-resolution edge flow approach to vascular ultrasound for intima-media thickness (IMT) measurement. In particular, this patent application discloses various embodiments of a computer-implemented system and method for intima-media thickness (IMT) measurements in the presence or absence of calcium at the near (proximal) wall of the arterial vessel. Although the embodiments disclosed herein are described in regard to particular blood vessels (e.g., carotid), the systems and methods disclosed and claimed are also applicable to IMT measurement in any blood vessel in any living organs or tissue. For example, various embodiments can be used for IMT measurement in carotid, femoral, brachial and aortic arteries. The details of various example embodiments are provided herein.

Overview of Various Embodiments

In the various example embodiments described herein, a variety of benefits and advantages are realized by the disclosed systems and methods. A representative sample of these advantages is listed below.

A. Coarse to Fine Resolution Processing: Previous art has focused on methods for either classification of media layer or finding the MA edges in the manual designated region of interest (ROI). Since it is manual ROI, it is time consuming and non-practical for clinical applications, we have developed a new method which is fast, accurate, reliable and very practical for IMT measurement for carotids, brachial, femoral and aortic blood vessels. Since the manual methods are time consuming and requires a lot of training, this applications is a two step stage process: (a) automated artery recognition and (b) automated calibration which finds the LIMA borders more accurately. The automated recognition process is hard given the Jugular vein in the neighborhood. Our concept is to recognize the artery in a smaller image with a high speed (so-called coarse resolution) and spot the artery out. The spotted artery can then be seen in the fine resolution or high resolution. This will allow processing the pixels in the correct region of interest. The statistics of the neighboring pixels will not affect the region of interest, which is where the accurate LIMA borders need to be determined. Normally, arteries are about 10 mm wide while the media thickness is about 1 mm wide. It is also known from our experience that the image resolution is about 15 pixels per mm. If we can bring the original resolution to a coarse resolution by one step down sample, we can bring the media layer to about 8 pixels per mm. Further, if this coarse resolution is down sampled by another half, then one can bring the image resolution from 8 pixels/mm to 4 pixels/mm. Thus, if the coarse resolution of the arterial ultrasound vessels has a medial thickness of 4 pixels/mm, one can detect such edges by convolving the higher order derivatives of Gaussian kernel with the coarse resolution image. Thus the new concept here is to automatically detect the arterial wall edges by down sampling the image and convolving the coarse images to higher order derivatives of Gaussian kernels. This allows the media layer to be automatically determined. Such an approach for automated media layer detection from fine to coarse resolution will further improve the region of interest determination. The art of changing the fine to coarse resolution has been popular in computer vision sciences. There are several methods available to converting the image from high resolution to coarse resolution. One of them is wavelet-based method where wavelets are being applied for down sampling the image to half. Another method can be hierarchical down sampling method using Peter Burt's algorithm. Thus the first advantage of the current system is automated recognition of the artery at coarse resolution and then using the MA border for visualization and recognition at the fine resolution (up-sampled resolution). This scheme has several advantages to it:
  (1) Robustness and Accurate Wall Capture: it is very robust because the higher order derivative kernels are very good in capturing the vessel walls (see, A Review on MR Vascular Image Processing Algorithms: Acquisition and Pre-filtering: Part I, Suri et al., IEEE TRANSACTIONS ON INFORMATION TECHNOLOGY IN BIOMEDICINE, VOL. 6, NO. 4, pp. 324-337, December 2002; and A Review on MR Vascular Image Processing: Skeleton Versus Nonskeleton Approaches: Part II, Suri et al., IEEE TRANSACTIONS ON INFORMATION TECHNOLOGY IN BIOMEDICINE, VOL. 6, NO. 4, December 2002).
  (2) Easter than the conventional processing: Since the recognition is strategized at coarse level down sampled twice from its original size of the image, it is therefore processing $\frac{1}{4}^{th}$ the number of pixels for automated recognition of the media layer. This improves the speed of the system.
  (3) Independent of Orientation of the vascular scan: Another major advantage to the system is that these Gaussian kernels are independent of the orientation of the blood vessels in the image. Since the ultrasound vascular scans do not always have the vessel orientation horizontal with respect bottom edge of the image, manual methods can pose a further challenge towards the region of interest estimation.
  (4) Guiding Method for the Calibration System: Since the recognition is followed by the calibration process, the calibration system becomes very robust since the calibration processing is done in the region of interest determined by the automated recognition system. Thus the calibration system adds the value determined by the automated recognition system for vascular ultrasound such as IMT measurement for carotid, femoral, aortic and brachial. Such a combination where the calibration system is guided by the automated recognition system helps in mass processing of huge databases.
  (5) Running the Mass IMT system for clinical Analysis: Since the recognition is automated followed by the calibration system, the largest value such a system would deliver will be in its real time use for analysis of IMT measurement on a large databases. Running clinical databases on still images would be even more beneficial because such a system would be completely automated in terms of recognition and IMT measurement.
  (6) Applications: Since the ultrasound probes use almost the same frequency of operation for scanning the vascular arteries such as carotid, femoral, brachial and aortic, it is thus possible to use such a system for these blood vessels.

B. In the conventional art, we have seen that the speckle reduction has been used for removing speckles in the ultrasound images. Though speckle reduction is common in ultrasound imaging, but the way speckle reduction is used here is very conservative. The idea here is to find out where the LIMA borders are using automated recognition system and then apply the local statistical speckle reduction filter in specific set of pixels which come under the LIMA band or media layer. Such a strategy allows multiple advantages:
  (1) Avoiding Large Computation Times on Speckle Reduction: The computation time for speckle reduction is not wasted in such a strategy, unlike conventional methods, where the speckle reduction is part of the whole streamline flow and is being run on the whole image.
  (2) Speckle Reduction is implemented on the original raw intensity in the region estimated at a Coarse Resolution: Second, the speckle reduction filter is run in the automated recognized region (MA borders) which is actually applied on the original image rather than on the coarse image. This way the original speckles are removed preserving the intensities of high gradient structures like LI and MA peaks. This is very important because the calibration system acts on these speckle reduction region of interest.

(3) Guidance to the Calibration System: The calibration system is guided by the speckle reduction filter which is optimized for the region of interest.

C. Extracting LIMA borders in presence of Calcium Shadow: Calcium is an important component of the media layer. It is not exactly known how the calcium is formed, but it is said that calcium accumulates in the plaques. During the beginning of Atherosclerosis disease, the arterial wall creates a chemical signal that causes a certain type of WBC (white blood cells) such as monocytes and T cells that attaches the arterial wall. These cells then move into the wall of the artery. These T cells or monocytes are then transformed into foam cells, which collect cholesterol and other fatty materials and trigger the growth of the muscle cells (which are smooth in nature) in the artery. Over time, it is these fat-laden foam cells that accumulate into plaque covered with a fibrous cap. Over time, the calcium accumulates in the plaque. Often times, the calcium is seen in the near wall (proximal wall) of the carotid artery or aortic arteries. This causes the shadow cone formation in the distal wall (far wall). As a result the LI boundaries are over computed from its actual layer. The shadow causes the LI lining over the actual LI boundary. As a result, the LI-MA distances are over computed in the shadow zone. Because of this, the IMT formation is over computed in these cases.

The various embodiments described herein accurately process the IMT computation even in the presence of a shadow cone formation. As described in more detail herein, the actual LI boundaries are recovered if calcium is present causing the shadow cone. As a result, the IMT computation of the various embodiments has the following advantages when shadow cones are encountered.

(1) Accurate IMT computation in real time when the calcium is present in the proximal wall (near wall) causing the shadow cone formation; and (2) The system allows computing the IMT in both cases: (a) when calcium is present and when calcium is not present.

Brief Summary of Example Embodiments

In the various example embodiments described herein, a computer-implemented system and method for fast, reliable, and automated embodiments for using a multi-resolution edge flow approach to vascular ultrasound for intima-media thickness (IMT) measurement is disclosed. The completely automated technique described herein can be denoted as AtheroEdge, the AtheroEdge system, the AtheroEdge process, or the Edge Flow process. The AtheroEdge process of an example embodiment includes two steps: (i) the automated recognition of the carotid artery (CA) in the image frame, and (ii) the segmentation of the far CA wall. The automatically traced LI and MA profiles are used to measure the IMT.

Figure 16:
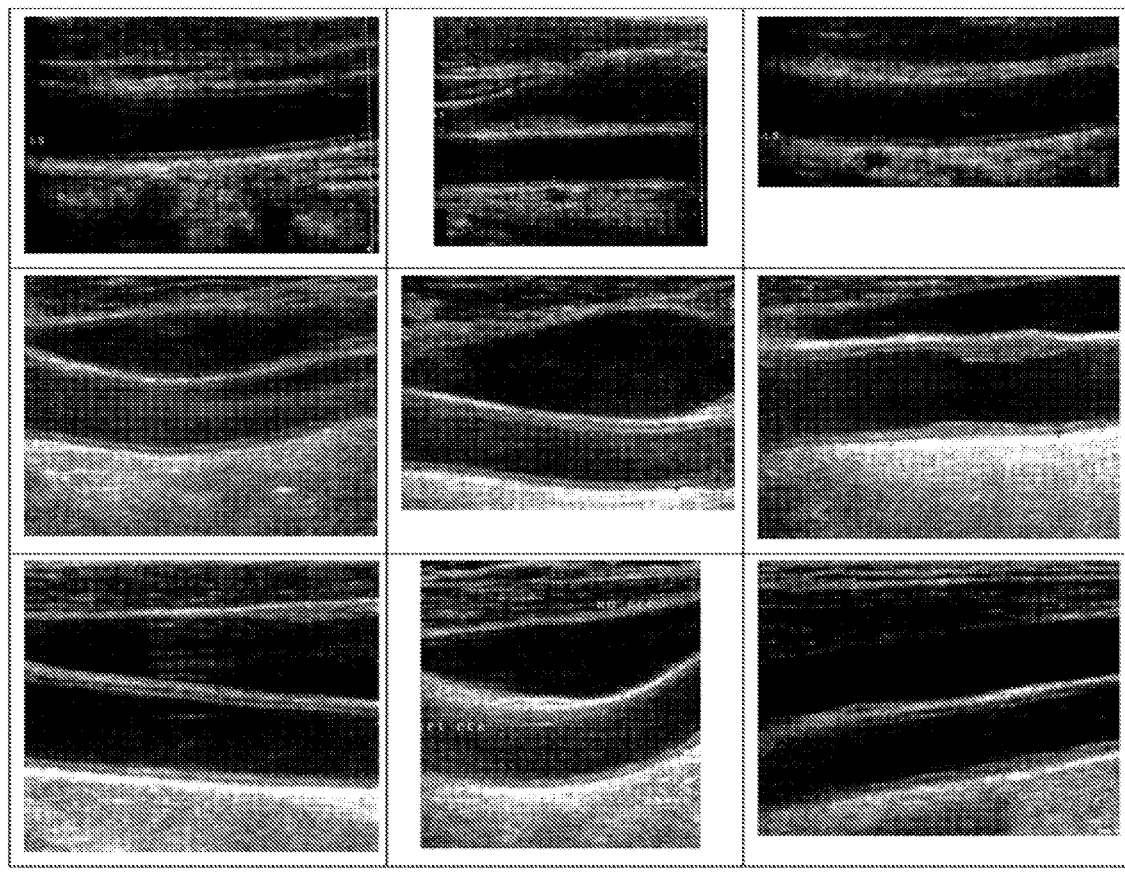
FIG. 16 shows the sample cropped images from our database.

Cropping System:

Preliminary, the raw ultrasound image is automatically cropped in order to discard the surrounding black frame containing device headers and image/patient data. If the image came in DICOM format (Digital Imaging and Communications in Medicine format), we relied on the data contained in the specific field named SequenceOfUltrasoundRegions, which contains four sub-fields that mark the location of the image containing the ultrasound representation. These fields are named RegionLocation (their specific label is xmin, xmax, ymin and ymax) and they mark the horizontal and vertical extension of the image. The raw B-Mode image is then cropped in order to extract only the portion that contains the carotid morphology. Those skilled in the art of DICOM will know that if the image came in from other formats or if the DICOM tags were not fully formatted, one can adopt a gradient-based procedure. We computed the horizontal and vertical Sobel gradient of the image. The gradients repeat similar features for the entire rows/columns without the ultrasound data: they are zero at the beginning and at the end. Hence, the beginning of the image region containing the ultrasound data can be calculated as the first row/column with gradient different from zero. Similarly, the end of the ultrasound region is computed as the last non-zero row/column of the gradient. FIG. 16 shows the automated cropped images.

Automatic Recognition of the CA:

To automatically identify the CA in the image frame, we developed a novel and low-complexity procedure. The following sample steps are used for automatic CA recognition, starting with the automatically cropped image which constitutes the input of the procedure.

Figure 18:
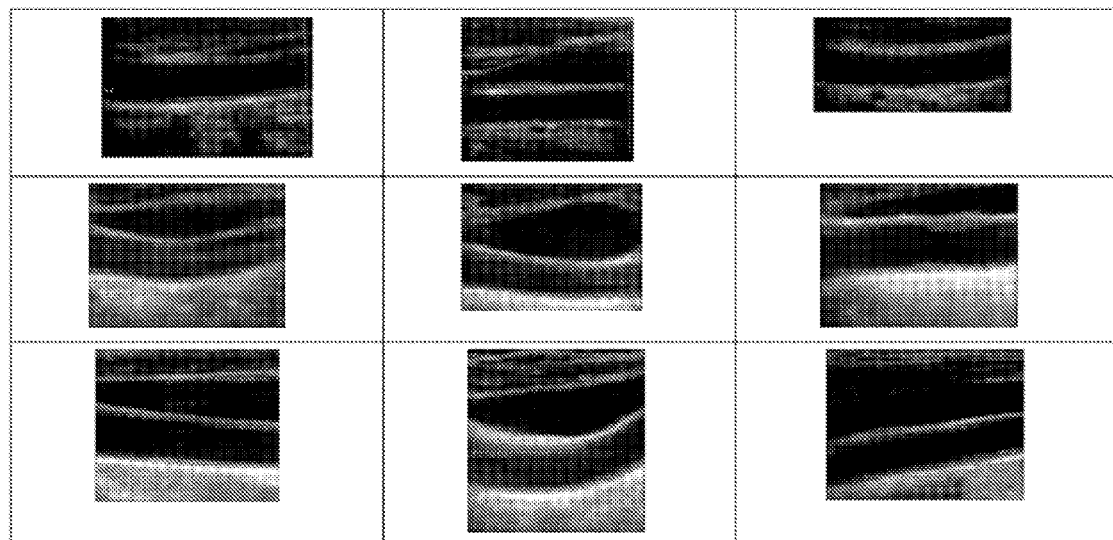
FIG. 18 shows the down sampling results.

Downsampling. The image was first down-sampled by a factor of 2 (i.e., the number of rows and columns of the image was halved). FIG. 18 shows the automated cropped images.

Speckle reduction. Speckle noise was attenuated by using a first-order statistics filter, which gives satisfactory performance in the specific case of carotid imaging. This filter is defined by the following equation:

$$J_{x,y} = \bar{I} + k_{x,y}(I_{x,y} - \bar{I}) \quad (1)$$

where, $I_{x,y}$ is the intensity of the noisy pixel, $\bar{I}$ is the mean intensity of a N×M pixel neighborhood and $k_{x,y}$ is a local statistic measure. The noise-free pixel is indicated by $J_{x,y}$.

Figure 17:
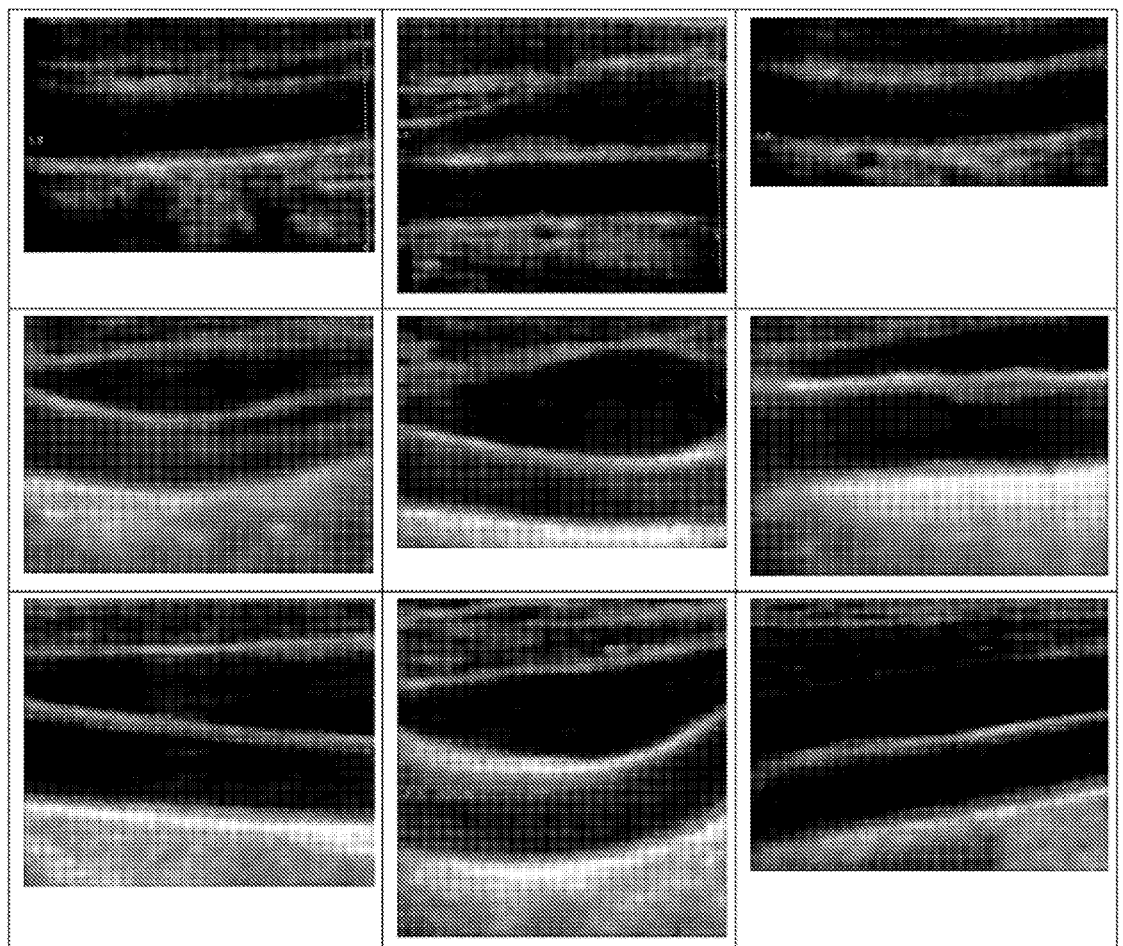
FIG. 17 shows the de-speckled filter.

As conventionally known, $$k_{x,y} = \frac{\sigma_I^2}{\bar{I}^2 \sigma_I^2 + \sigma_n^2},$$

where $\sigma_I^2$ represents the variance of the pixels in the neighborhood, and $\sigma_n^2$ the variance of the noise in the cropped image. An optimal neighborhood size was shown to be 7×7. FIG. 17 shows the automated cropped images.

Higher order Gaussian derivative filter. The despeckled image was filtered by using a first order derivative of a Gaussian kernel filter. It is possible to observe how the CA walls become enhanced to white. The sigma parameter of the Gaussian derivative kernel was taken equal to 8 pixels, i.e. to the expected dimension of the IMT value. In fact, an average IMT value of say 1 mm corresponds to about 16 pixels in the original image scale and, consequently, to 8 pixels in the down-sampled scale.

Figure 19:
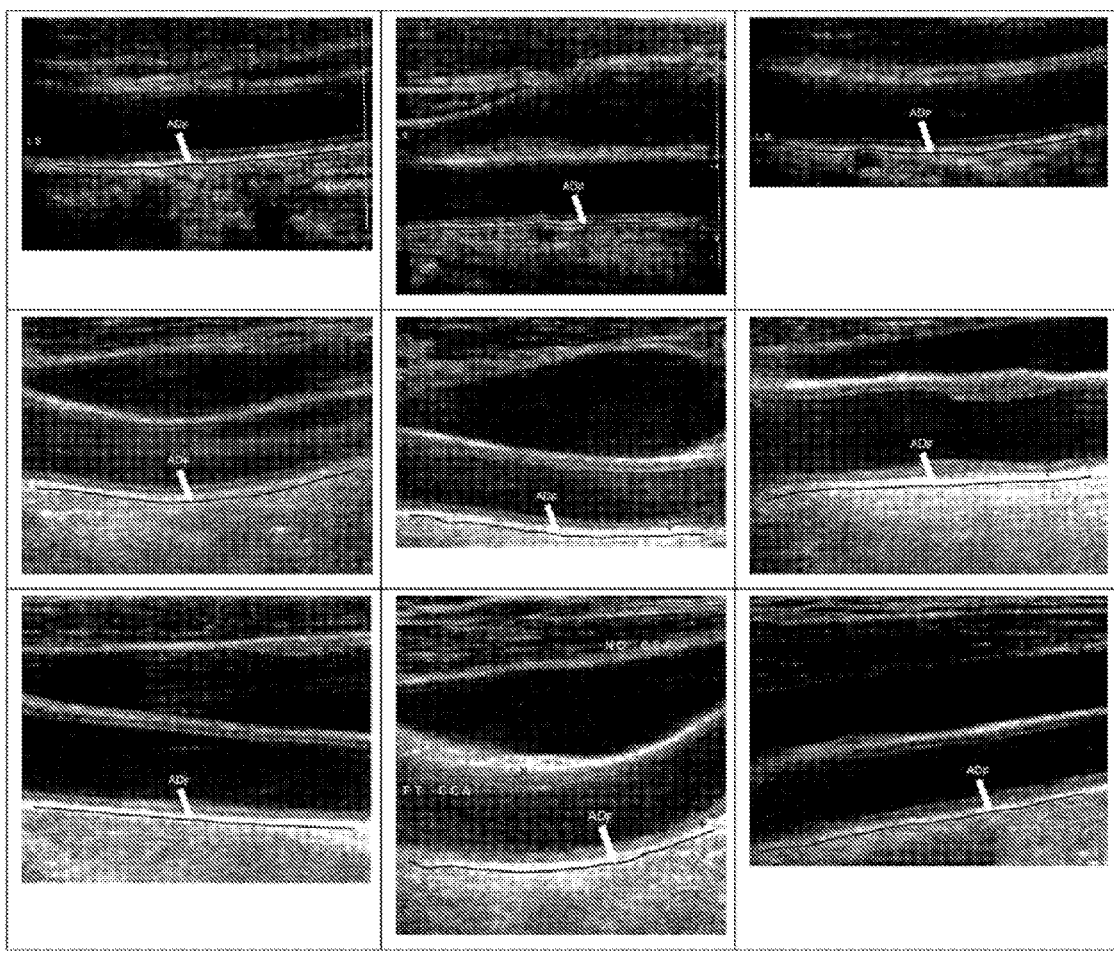
FIG. 19 shows artery recognition phase of the Adventitia.

Far adventitia automated tracing. To automatically trace the profile of the far wall, we used a heuristic search applied to the intensity profile of each column. Starting from the bottom of the image (i.e. from the pixel with the higher row index), we searched for the first white region of at least 6 pixels of width. The deepest point of this region (i.e. the pixel with the higher row index) marked the position of the far adventitia ($AD_F$) layer on that column. The sequence of all the points of the columns constituted the overall $AD_F$ automatically generated tracing. FIG. 19 shows the automated cropped images.

Up-sampling. The $AD_F$ profile was up-sampled to the original scale and overlaid to the original image. At this stage, the CA far wall is automatically located in the image frame and automated segmentation is made possible.

Figure 20:
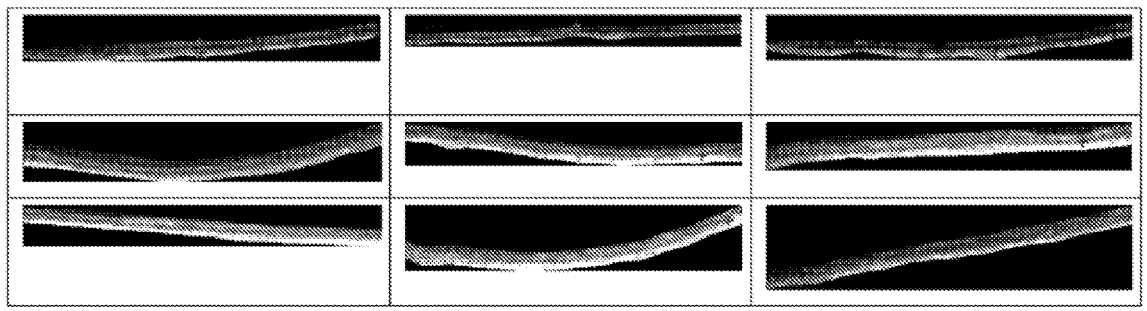
FIG. 20 shows the Guidance Zone.

Stage II (Calibration Phase, Guidance Zone Creation):

Stage II is started by the automatic extraction of a Guidance Zone Mask, which is found starting from the ADF profile and extending towards the upper edge of the image by 50 pixels. The original image is then cropped with the smallest rectangle possible that includes the entire Guidance Zone Mask (see FIG. 20). Consequently, the Edge Flow process is run on the cropped image to obtain the initial edges.

Detailed Description of Example Embodiments

This patent application discloses various embodiments of a computer-implemented system and method for fast, reliable, and automated embodiments for using a multi-resolution edge flow approach to vascular ultrasound for intima-media thickness (IMT) measurement. In particular, this patent application discloses various embodiments of a computer-implemented system and method for intima-media thickness (IMT) measurements in the presence or absence of calcium at the near (proximal) wall of the arterial vessel. Although the embodiments disclosed herein are described in regard to particular blood vessels (e.g., carotid), the systems and methods disclosed and claimed are also applicable to IMT measurement in any blood vessel in any living organs or tissue. For example, various embodiments can be used for IMT measurement in carotid, femoral, brachial and aortic arteries. The details of various example embodiments are provided herein.

In the following description, for purposes of explanation, numerous specific details are set forth in order to provide a thorough understanding of the various embodiments. It will be evident, however, to one of ordinary skill in the art that the various embodiments may be practiced without these specific details.

This patent application discloses a computer-based system and method for intima-media thickness (IMT) measurements in presence of calcium or absence of calcium in near (proximal) end of the arterial value. The embodiment is useful for the measurement of the carotid, femoral, brachial and aortic arteries. IMT measurement is a very important risk marker of the Atherosclerosis disease. Typically, there are two ways to measure the arterial IMT's: (a) invasive methods and (b) non-invasive methods. In invasive methods, traditionally, intravascular ultrasound (IVUS) is used for measuring vessel wall thickness and plaque deposits where special catheters are inserted in the arteries to image them. Conventional ultrasound is used for measuring IMT non-invasively, such as from carotid, brachial, femoral and aortic arteries. The main advantages of non-invasive methods are: (i) low cost; (ii) convenience and comfort of the patient being examined; (iii) lack of need for any intravenous (IV) insertions or other body invasive methods (usually), and (iv) lack of any X-ray radiation; Ultrasound can be used repeatedly, over years, without compromising the patient's short or long term health status. Though conventional methods are generally suitable, conventional methods have certain problems related to accuracy and reliability.

The IMTs are normally 1 mm in thickness, which nearly corresponds to 15 pixels on the screen or display. IMT estimation having a value close to 1 mm is a very challenging task in ultrasound images due to large number of variabilities such as: poor contrast, orientation of the vessels, varying thickness, sudden fading of the contrast due to change in tissue density, presence of various plaque components in the intima wall such as lipids, calcium, hemmorage, etc. Under normal resolutions, a 1 mm thick media thickness is difficult to estimate using stand-alone image, processing techniques. Over and above, the image processing methods face an even tighter challenge due to the presence of speckle distribution. The speckle distribution is different in nature from these interfaces. This is because of the structural information change between intima, media and adventitia layers of the vessel wall. As a result, the sound reflection from different cellular structures is different. The variability in tissue structure—all that happens in 1 mm of the vessel wall—brings fuzziness in the intensity distribution of the vessel wall. Under histology, media and adventitia walls are clearly visible and one can observe even their thicknesses. This 1 mm zone is hard to discern in a normal resolution image of 256×256 pixels in a region of interest (ROI) or in a higher resolution image of 512×512 pixels in a region of interest (ROI). One needs a high resolution image to process and identify the intensity gradient change in ultrasound images from lumen to intima and media to adventitia layers. The ultrasound image resolution may not be strong enough like MRI or computerized axial tomography (CAT or CT) images, which can be meaningful for soft tissue structural information display.

There are two ways to process and identify the intensity gradient change in ultrasound images from lumen to intima (LI) and media to adventitia (MA) layers: (a) have a vascular surgeon draw the LI/MA borders and compute the IMT image interactively, OR (b) have a computer determine the LI and MA borders along with IMT's. Case (a) is very subjective and introduces variability in the IMT estimation. IMT screenings are really part of the regular check-up for patients and millions of scans are done each day around the world. The manual handling of such a repetitive work flow of IMT screenings is tedious and error-prone. Case (b) is difficult to implement, because it is difficult to identify the LI and MA borders with heavy speckle distribution and the inability of ultrasound physics to generate a clear image where the semi-automated or automated image processing methods are used for IMT estimation. Besides that, the calcium deposit in the near walls causes the shadow. The worst is that there are gaps along the lumen-intima (LI) borders and media-adventitia (MA) borders. These gaps bring non-continuity in the segmentation process and pose a challenge in the IMT measurement.

Figure 3:
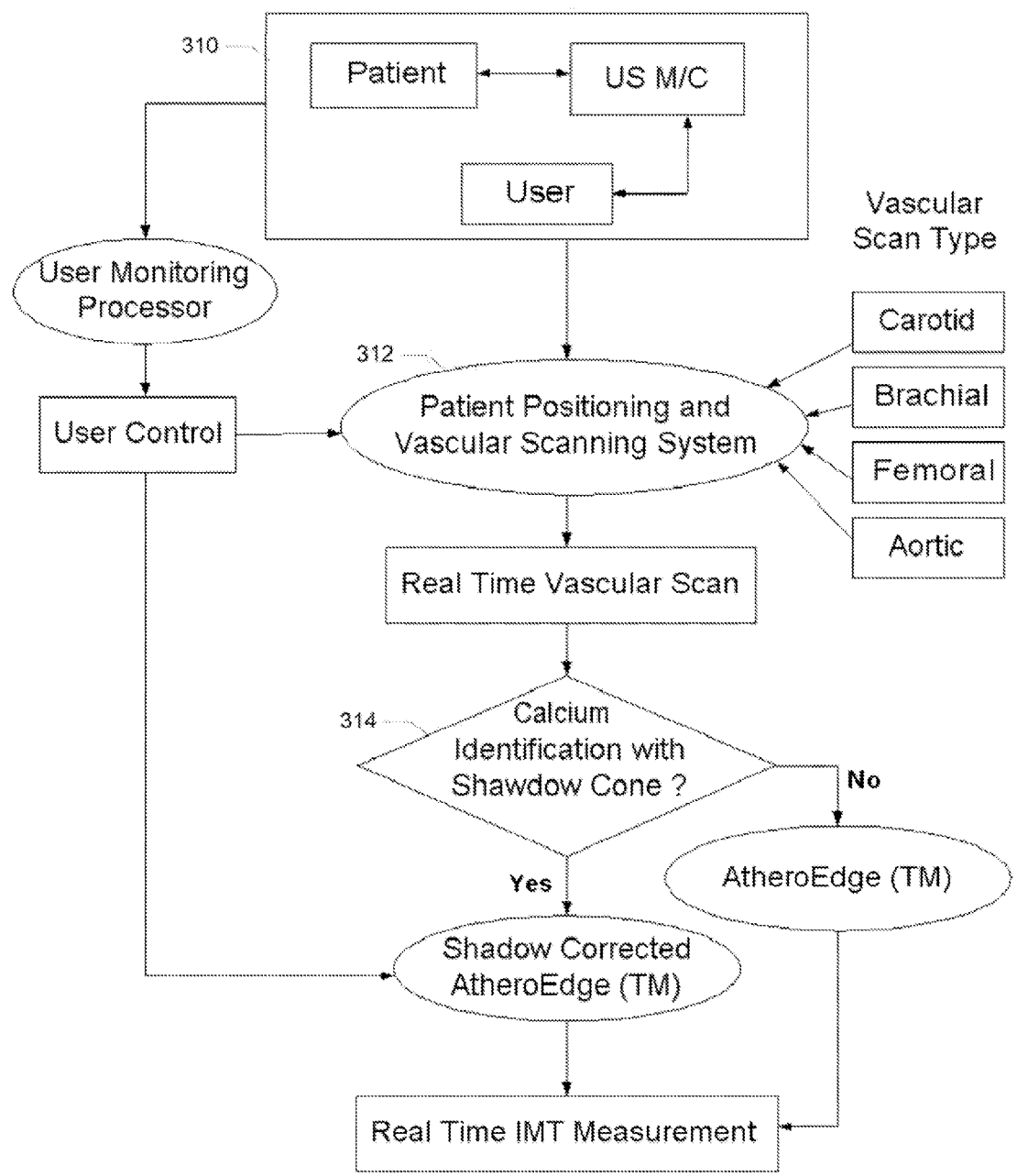
FIG. 3 shows the overall system of an example embodiment, which can be applied for computation of the IMT for any kind of vascular ultrasound data such as coming from Carotid, Brachial, Femoral and Aortic.

FIG. 3 shows the OPD (object process diagram) for the whole system of an example embodiment. The top box 310 shows the interacting system between ultrasound machine, patient and user. The various embodiments are applicable to vascular ultrasound for carotid, brachial, aortic and femoral but not limited to these alone. For carotid, one can use the left and the right scan. When the patient comes in, the system is made to get ready for the ultrasound scan and IMT measurement. Patient is positioned optimally for the best scan and then gel is applied before vascular scanning. The probe is then skin surfaced for the carotid scan as seen in the FIGS. 1A and 1B. The first sub-system 312 in FIG. 3 shows the patient positioning and vascular scanning system. The input to this block is vascular scan type: carotid, brachial, femoral and aortic, which means these four different kinds of arteries, can be used for IMT measurement. The output to the system is the real time ultrasound vascular scan, normally DICOM in format. In the FIG. 3 is also shown that the user completely monitors the system all the time and is in user's control all the time. This allows for perfect synchronization of the patient interface with ultrasound and for the diagnostic IMT measurement system. Normally, the vascular screening is done by the vascular surgeon, neuroradiologist, sonographer, or cardiologist. They are trained to recognize any calcium present near the proximal wall zone. The diamond box 314 shows if the calcium is present in arterial wall or not. The user such as neuroradiologist, sonographer, cardiologist, or vascular surgeon uses his/her expertise to spot the calcium and its shadow in the proximal (near) end of the arterial wall. Those skilled in the art will note that even though the probe is used longitudinally in B-mode for scanning the arterial wall, one can change the orientation of the probe orthogonal to the blood flow and move the probe linearly along the carotids or brachial or femoral or aortic to get the transverse slices to see the extent (range) of the calcium.

Since the presence of the calcium in longitudinal B-mode scans causes the calcium cone in the ultrasound images, a different processing stage is required before the AtheroEdge™ stand alone process is applied for IMT measurement. The AtheroEdge™ system is made to activate if there is no calcium is present while AtheroEdge™ system with calcium correction is made to activate when calcium is spotted in the longitudinal or transverse B-mode images. The output of the AtheroEdge™ process (with or without calcium system) is the real time IMT measurement. Note that the user completely monitors the system all the time and is in user's control all the time during the AtheroEdge™ system operation with calcium and AtheroEdge™ system operation without calcium.

Figure 1B:
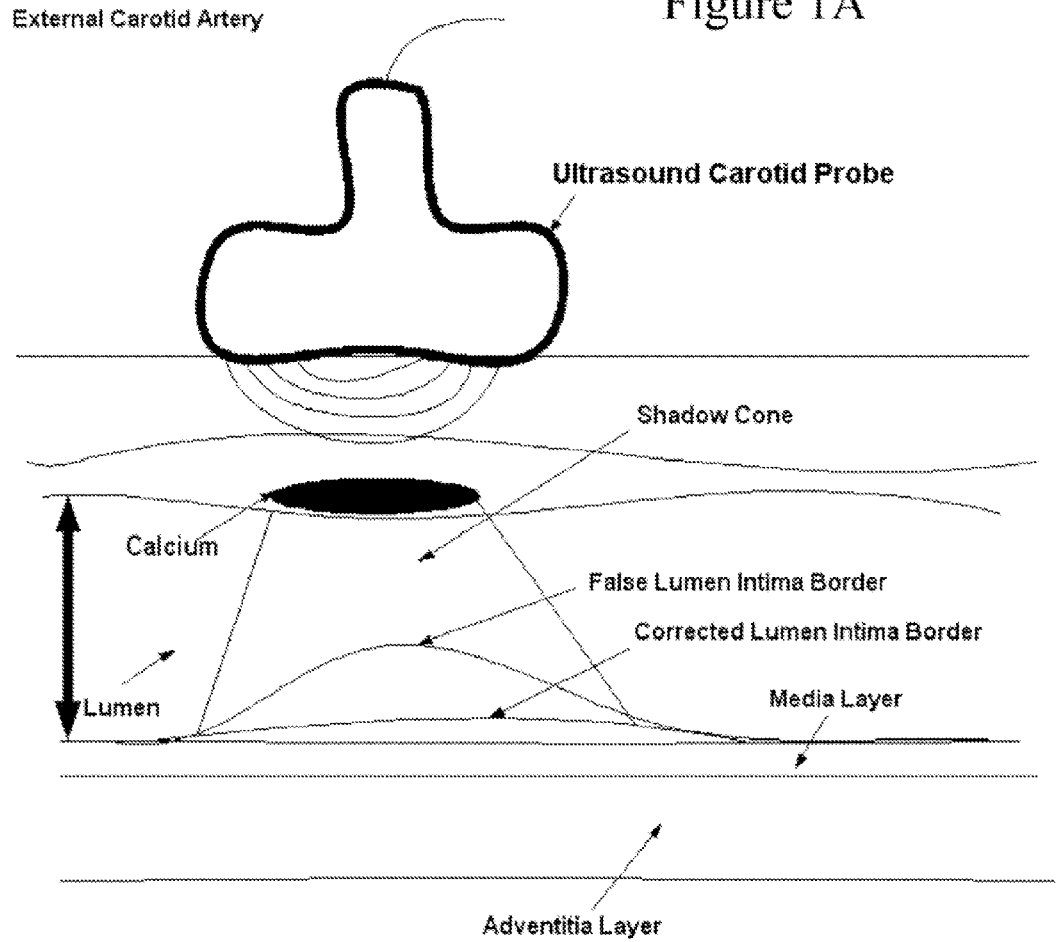
FIG. 1B shows the calcification seen in the proximal wall (near wall) of the ICA and its corresponding shadow.
Figure 2:
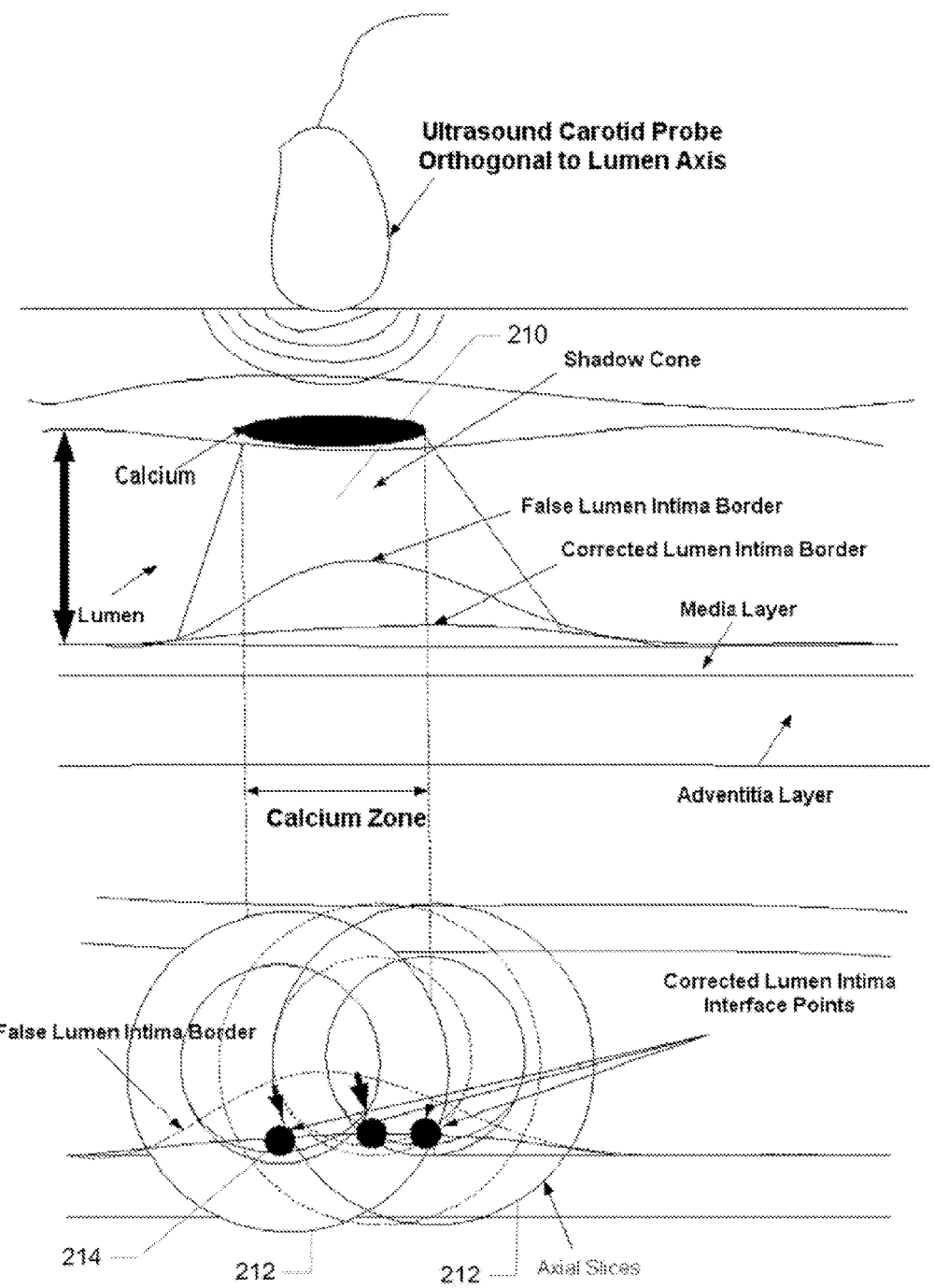
FIG. 2 shows the solution of the calcification issue, where the transverse slices are acquired instead of B-mode longitudinal images. These transverse slices are depicted as circular cross-sectional in the image.

FIG. 1B and FIG. 2 show the diagrammatic view where calcium is present in the proximal wall. As can be seen in the figure a black region in the image in intima layer or media layer or in the lumen region but hanging from the intima layer. There are many variability of how the calcium can stick or hang in the proximal wall, but in every case, there will be a shadow caused when ultrasound is blocked by this calcium present in the arterial wall (see the details by Robin Steel et al., Origins of the edge shadowing artifact I medical ultrasound imaging, Ultrasound in Med. & Biol., Vol. 30, No. 9, pp. 1153-1162, 2004). It has been shown that calcification causes echogenity in the ultrasound image to be hypoechoic (darker) and covers the true reflection coming out of the media layer of the distal (far) borders. Okuda et al. showed these kinds of hypoechoic zones in the ultrasound images due to the presence of calcium in the renal arteries (see, Okuda et al., Sonographic Features of Hepatic Artery Calcification in Chronic Renal Failure, Acta Radiologica 44, 2003. 151-153). IMT measurements in such cases can become difficult or challenging. This application just not finds the reliable and automated IMT measurements in ordinary arterial walls, but also in the presence of calcification. FIG. 2 shows the calcification of the proximal end of the wall and the shadow cone made by the calcification and projected onto the distal (far) end of the wall. Due to this as shown in the figure, the LI borders are over calculated or wrongly calculated. It is shown in the figure that using the techniques described herein, we can correct the LI borders for the distal (far) end of the wall. This correction has to be applied in the region where calcification is present.

Thus, we also disclose a method, which can actually compute the IMT values if the user (cardiologist, neuroradiologist, vascular surgeon, sonographer) does not find the calcium shadows. We provide a reliable, real time and accurate method for IMT measurement when there is no calcium present. Similarly, we provide a method to find IMT when the calcium is present. When calcium is not present, the IMT computation uses the AtheroEdge™ system directly, but when calcium is present the system uses the AtheroEdge™ process in the non-calcium zones and correcting the LI border in the calcium zones and then interpolating with the LI border of the non-calcium zone thereby getting the complete and correct LI borders.

FIG. 2 shows the methodology used for correcting the LI borders when the calcium shadow cones 210 are present. The method uses a combination of data acquisition and software method for correcting the LI borders. These two steps are done in real time while the probe is still sitting on the patient's artery. The combinational approach requires no change by the expert user (cardiologist, neuroradiologist, vascular surgeon, sonographer) who has been trained to use the probe on arterial anatomy. The holding method of using the probe still uses the same art by making the grip of four fingers and one thumb. The only change the user has to do is rotate his wrist 90 degree to the longitudinal axis. Once the calcium region is identified, the user (cardiologist, neuroradiologist, vascular surgeon, sonographer) rotates the orientation of the probe by rotating its wrist and taking the scans of the distal (far) wall. Since the probe is oriented orthogonally to the longitudinal axis of the arterial vessel, the images captures are axial or transverse in nature. The user then moves the probe with a reasonable speed linearly and while moving the probe, the transverse images are captured. The user can stop the linear movement of the probe as soon as the calcium region finishes.

These axial slices 212, captured with the probe oriented orthogonally to the longitudinal axis of the arterial vessel, will show the vessel wall which is circular band in nature. The inner wall shows the lumen region and outer wall is the adventitia walls. Since we are interested in the distal (far) walls in longitudinal B-mode, we look for the vessel wall region in the distal area of the artery. Those skilled in the art of doing 3D ultrasound will notice that the lumen region is dark (black) and the vessel wall (relatively brighter than lumen region), hence the interface region is discernable between lumen and walls. This change in gradient information for the distal (far) wall for that particular slice will allow the user manually or semi-automatically or automatically to estimate the gradient change between the lumen and vessel wall for that orthogonal slice. FIG. 2 shows the circular wall boundaries of the lumen and media-adventitia layers in axial or transverse slices 212. The point of gradient change between the lumen and vessel wall corresponding to the longitudinal B-mode position of the probe, orthogonal to the arterial axis is the point, which corresponds to the LI border where calcium region was hit. This point 214 is shown as a black circle in FIG. 2. Those skilled in the art of boundary estimation can use off the shelf snake method or deformable method or edge detection method to find the lumen boundary in the transverse slice of the ultrasound arterial image. The above process of finding the point of intersection of the longitudinal B-mode position to the circular vessel wall in the transverse image is repeated for all the transverse slices where calcium region is identified. The information extracted for the shadow region is stored to be reused because that is the partial information on the LI border. The rest of the information will be extracted from the AtheroEdge™ process using the longitudinal B-mode vascular ultrasound image.

Figure 4:
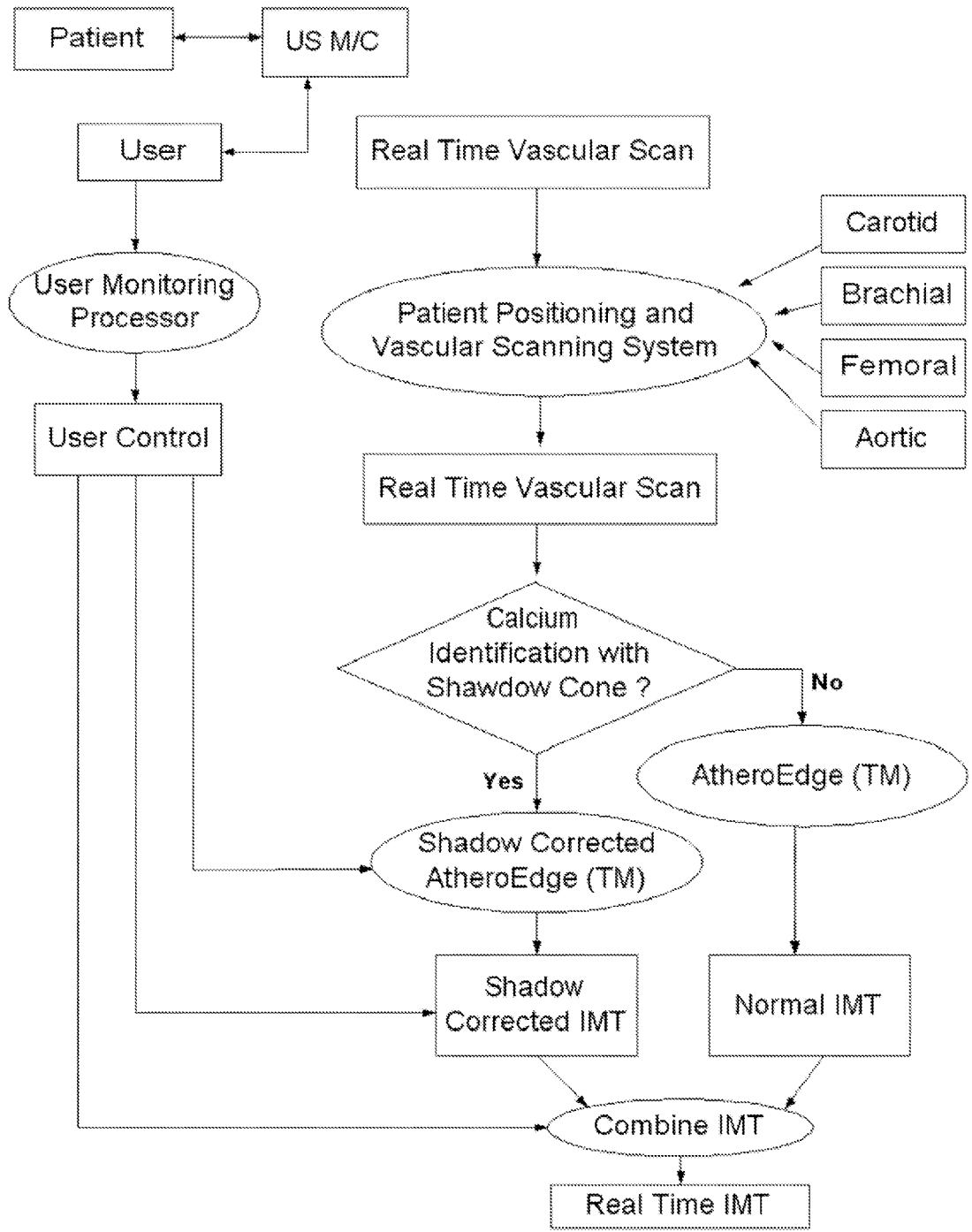
FIG. 4 shows the IMT values are combined with and without shadow cones. If there are no shadow cones (or calcium present), then the processes simply compute the real time IMT.

FIG. 4 actually shows the system which helps in combining the corrected LI boundary information from the calcium shadow zone (a shadow corrected AtheroEdge™ process) and LI boundary information for the non-calcium shadow zone. This will lead to the formation of the full LI boundary and MA boundary leading to the distance measurement called IMT. This can be seen in the FIG. 4. During the complete process, we must ensure that user in full control as a fall back system should the automated system encounters a challenge, there by changing to the semi-automated system. If the user (cardiologist, neuroradiologist, vascular surgeon, sonographer) does not encounter the calcium shadow, then, the plain automated AtheroEdge™ process will run for the IMT measurement.

Figure 5:
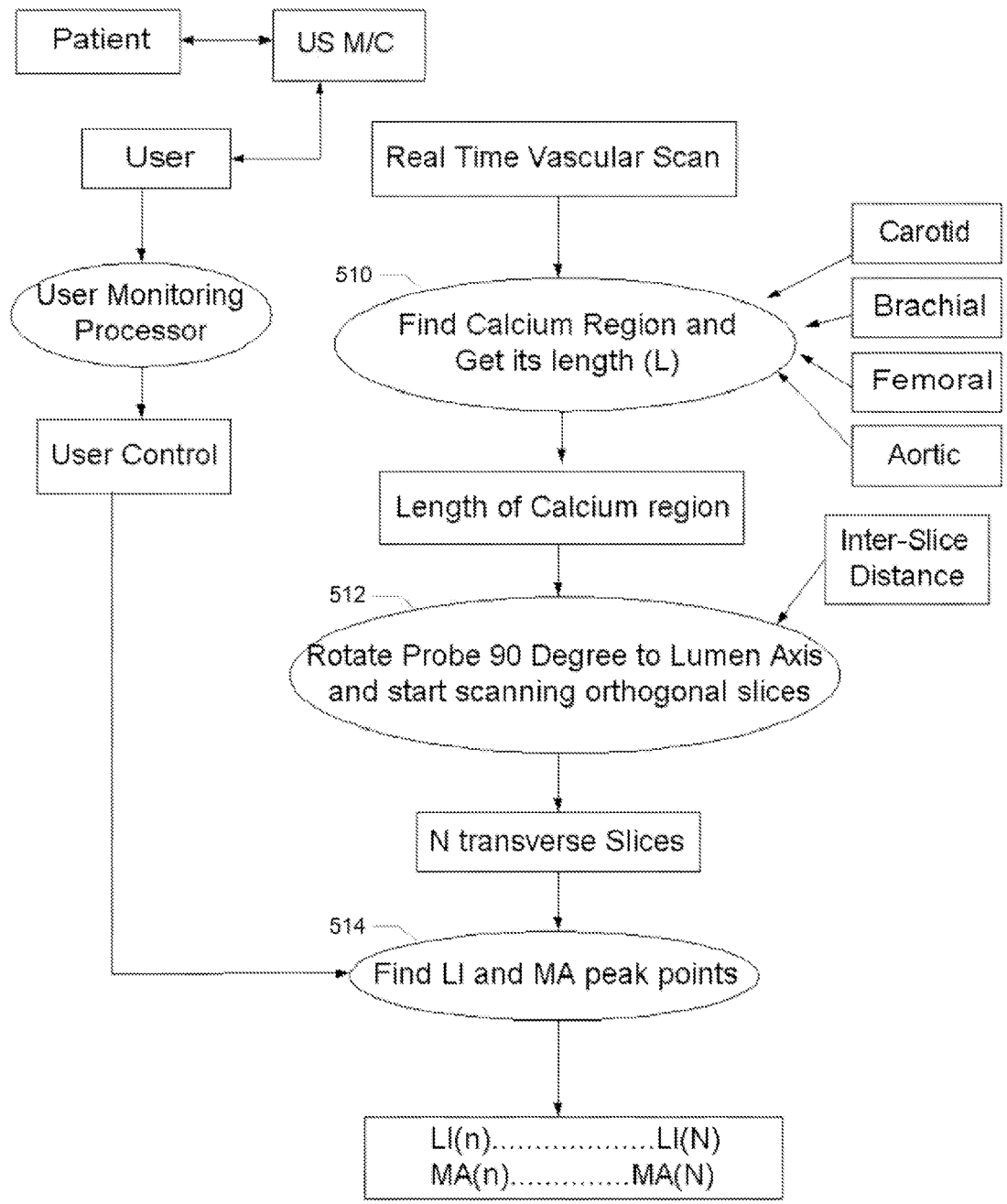
FIG. 5 shows data acquisition when the calcium is found in the proximal wall of the CCA/ICA during the ultrasound scans. The figure shows how the calcium zone is estimated in the proximal wall, then, how the probe orientation is changed to collect the transverse slices in the calcium zone. Finally, the figure shows how the LIMA points are determined in the transverse slices.

FIG. 5 shows how the system for computing the LI and MA boundaries in the calcium shadow zone, which is related to FIG. 2. The main components are the length of calcium zone estimation 510, acquiring the N transverse slices 512, and then estimating the LI boundary points corresponding to the shadow zone 514. Those of ordinary skill in the art of 3D ultrasound acquisition will notice that the inter-slice distance is important during the scanning process. In our methodology, it is not very critical information as we are only interested in limited number of points corresponding to the calcium zone.

Figure 6:
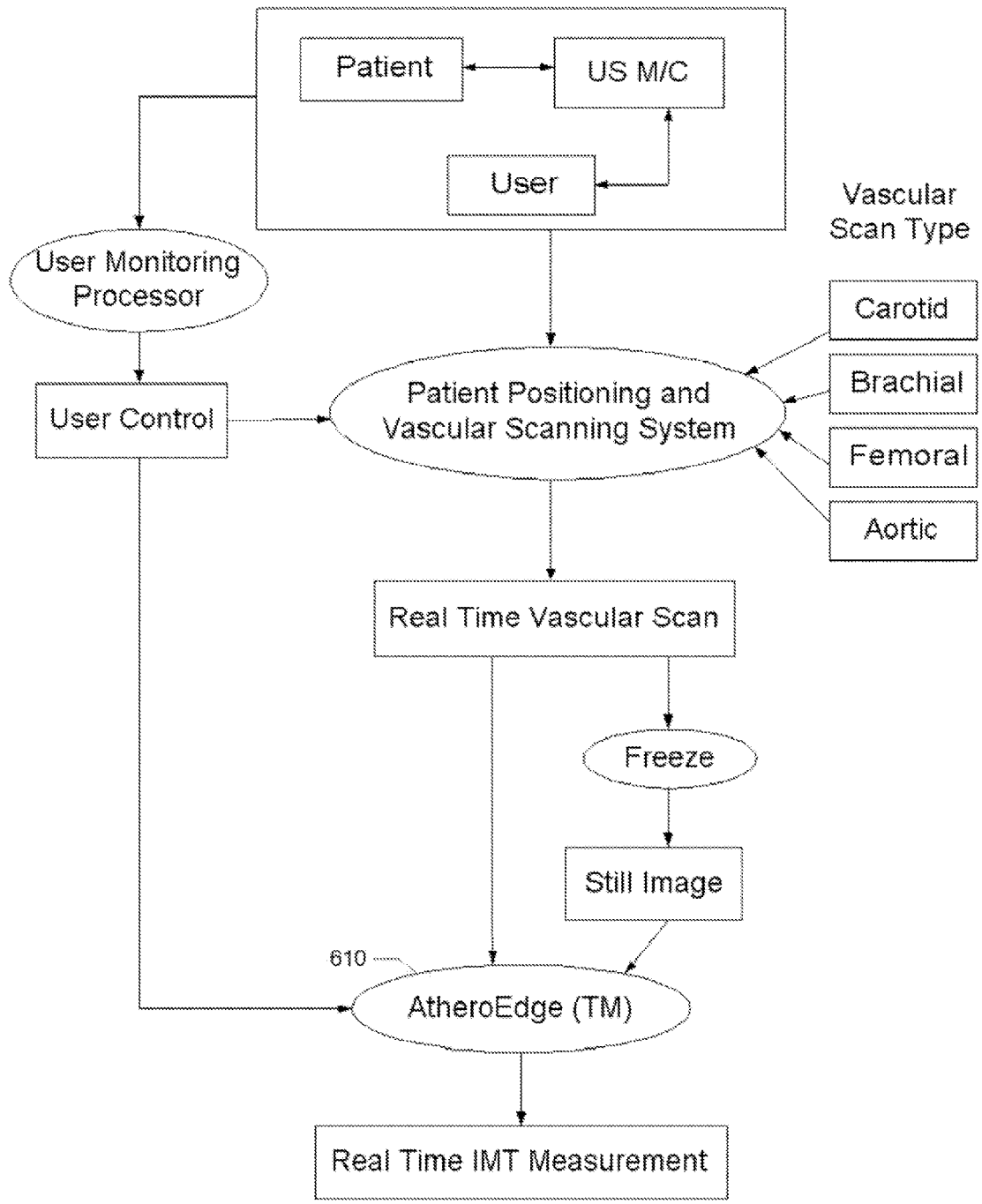
FIG. 6 shows how the system of various embodiments works given the still image of the B-mode longitudinal image of carotid or how the system of various embodiments works given the real time image of the B-mode longitudinal image of the carotid artery.

FIG. 6 shows the system where the AtheroEdge™ process 610 is being used in normal cases where there is no calcium shadow. The system shows how the ultrasound vascular image is acquired using the longitudinal B-mode process. The input to the system also shows that this process can take any of the four arteries: carotid, brachial, femoral and aortic. The system has ability to freeze the image as a still image, on which the IMT will be computed. User continuously monitors the process at all stages during the operation. User has control of the AtheroEdge™ software system, ultrasound machine, ultrasound probe, patient and the graphical user interface. The still image can be saved on the hard drive or compact disk (CD) drive. The still image can then also be transferred to an independent computer and the AtheroEdge™ process 610 can be run on that system as well. At the same time, the AtheroEdge™ process 610 can run real time while the patient is in the vascular screening room.

Figure 7:
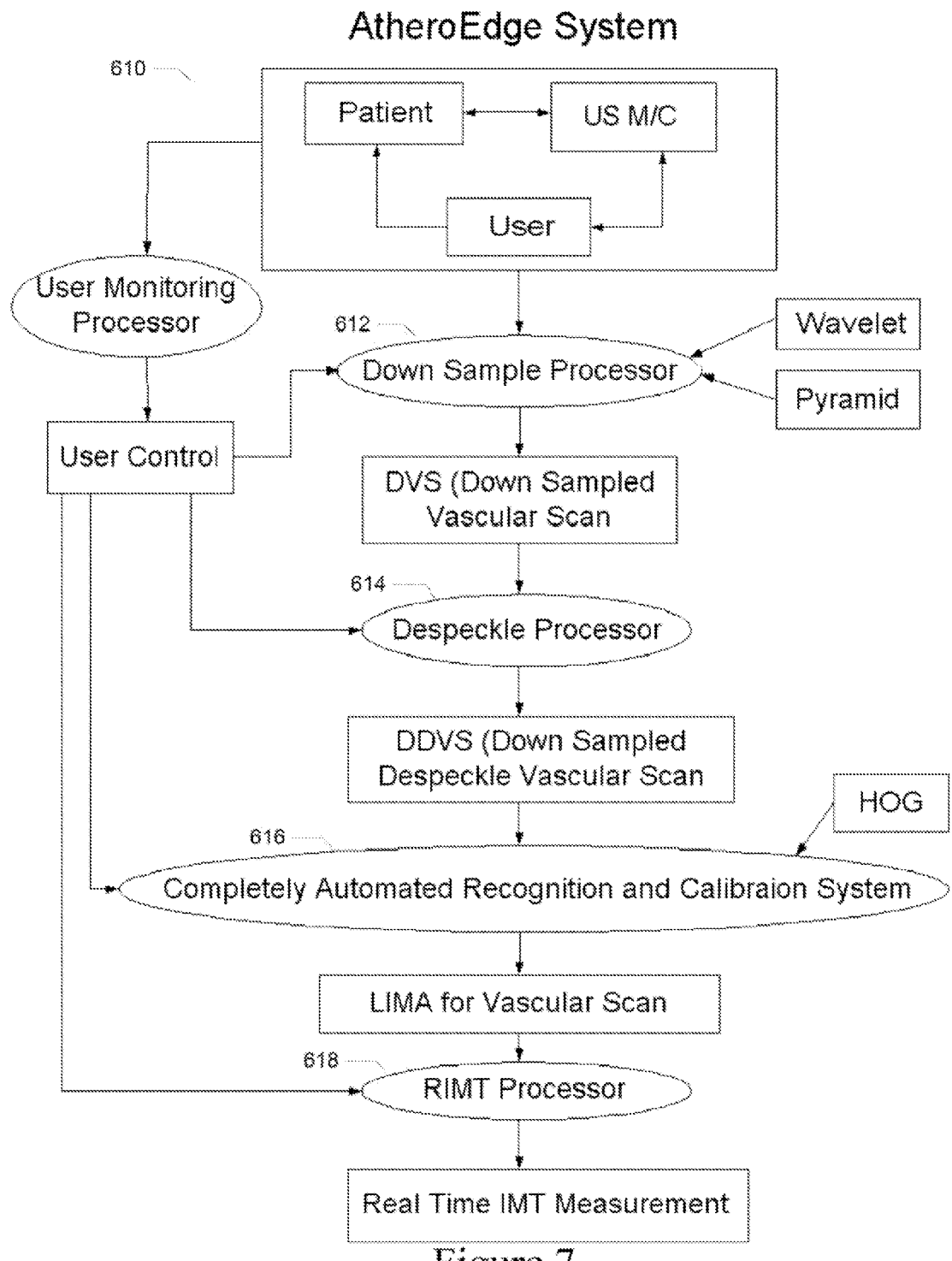
FIG. 7 shows the design of the system of various embodiments, which includes the following sub-systems: (a) down sample processor; (b) despeckle processor; (c) completely automated recognition and calibration system; and (d) Real-time IMT (RIMT) processor.

FIG. 7 shows the AtheroEdge™ system 610 where the main components of the system of an example embodiment are: (a) Multi-resolution Image Processor (also denoted Down Sample Processor) 612; (b) De-speckle Processor 614; (c) Recognition and Calibration Processor 616 and (d) RIMT Processor 618.

Figure 8:
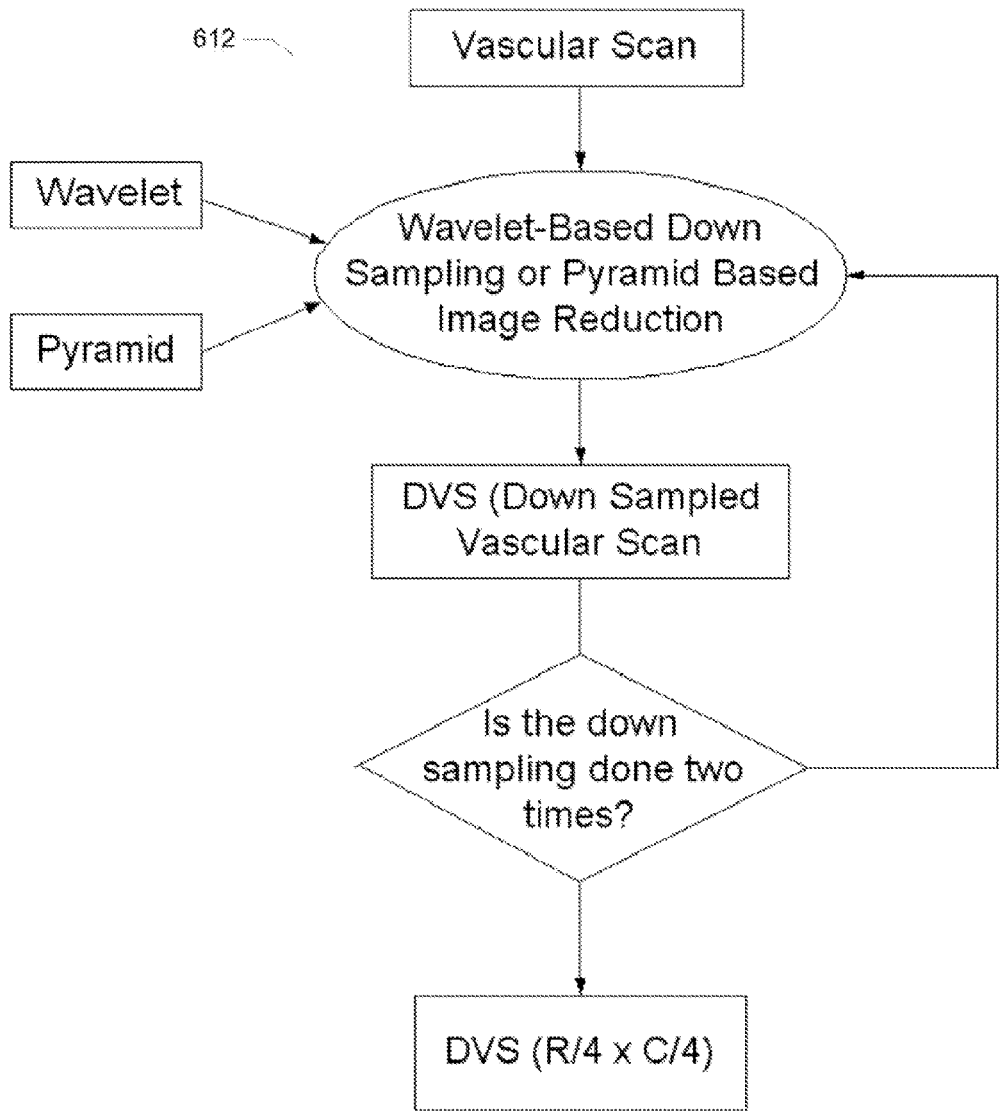
FIG. 8 shows the image reduction processor based on wavelet transform or pyramid filter, which can down sample the image two steps down.

Multi-resolution image processing yields the DSVS (down sampled vascular scan) image. FIG. 8 shows the down sampling or fine to coarse resolution system 612. One of the four systems can be used for fine to coarse sampling. The role of the multi-resolution process is to convert the image from fine resolution to coarse resolution. Those skilled in the art of down sampling can use any off-the-shelf down sampling methods. One of the very good down samplers is Lanczos interpolation. This is based on the sine function which can be given mathematically as:

$$\mathrm{sinc}(x) = \frac{\sin(\pi x)}{\pi x}.$$

Since the sine function never goes to zero, a practical filter can be implemented by taking the sine function and multiplying it by a "window", such as Hamming and Hann, giving an overall filter with finite size. We can define the Lanczos window as a sine function scaled to be wider, and truncated to zero outside of the main lobe. Therefore, Lanczos filter is a sine function multiplied by a Lanczos window. Three lobed Lanczos filter can be defined as:

$$Lanczos3(x) = \begin{cases} \dfrac{\sin(\pi x)\sin\left(\pi\dfrac{x}{3}\right)}{\pi x \cdot \pi\dfrac{x}{3}}, & \text{if } |x| \le 3 \\ 0, & \text{if } |x| > 3 \end{cases}$$

Although Lanczos interpolation is slower than other approaches, it can obtain the best interpolation results; because, the Lanczos method attempts to reconstruct the image by using a series of overlapping sine waves to produce what's called a "best fit" curve. Those skilled in the art of down sampling can also use Wavelet transform filters as they are very useful for multi-resolution analysis. The orthogonal wavelet transform of a signal f can be formulated by:

$$f(t) = \sum_{k \in z} c_j(k)\varphi_{j,k}(t) + \sum_{j=1}^{J}\sum_{k \in Z} d_j(k)\varphi_{j,k}(t)$$

where the $c_j(k)$ is the expansion coefficients and the $d_j(k)$ is the wavelet coefficients. The basis function $\phi_{j,k}(t)$ can be presented as:

$$\phi_{j,k}(t) = 2^{-j/2}\phi(2^{-j}t - k),$$

where k, j are translation and dilation of a wavelet function $\phi(t)$. Therefore, wavelet transforms can provide a smooth approximation of f(t) at scale J and a wavelet decomposition at per scales. For 2-D images, orthogonal wavelet transforms will decompose the original image into 4 different sub-band (LL, LH, HL and HH).

Bicubic interpolation can also be used as it will estimates the value at a given point in the destination image by an average of 16 pixels surrounding the closest corresponding pixel in the source image. Given a point (x,y) in the destination image and the point (l,k) (the definitions of l and k are same as the bilinear method) in the source image, the formulae of bicubic interpolation is:

$$f(x, y) = \sum_{m=l-1}^{l,2}\sum_{n=k-1}^{k,2} g(m \cdot n) \cdot r(m - l - dx) \cdot (dy - n + k).$$

where the calculation of dx and dy are same as the bilinear method. The cubic weighting function r(x) is defined as:

$$r(x) = \frac{1}{6}[p(x+2)^3 - 4p(x+1)^3 + 6p(x)^3 - 4p(x-1)^3],$$

where p(x) is:

$$p(x) = \begin{cases} x & x > 0 \\ 0 & x \le 0 \end{cases}$$

Bicubic approach can achieve a better performance than the bilinear method because more neighboring points are included to calculate the interpolation value.

Bilinear interpolator can also be used as it is very simple to implement. Mathematically, it is given as: if g represents a source image and f represents a destination image, given a point (x,y) in f, the bilinear method can be presented as:

$$f(x,y)=(1-dx)\cdot(1-dy)\cdot g(l,k)+dx\cdot(1-dy)\cdot g(l+1,k)+(1-dx)\cdot dy\cdot g(l,k+1)+dx\cdot dy\cdot g(l+1,k+1),$$

where $l=\lfloor x \rfloor$ and $k=\lfloor y \rfloor$, and the dx, dy are defined as dx=x−l and dy=y−k respectively. Bilinear interpolation is simple. However it can cause a small decrease in resolution and blurring because of the averaging nature.

Figure 9:
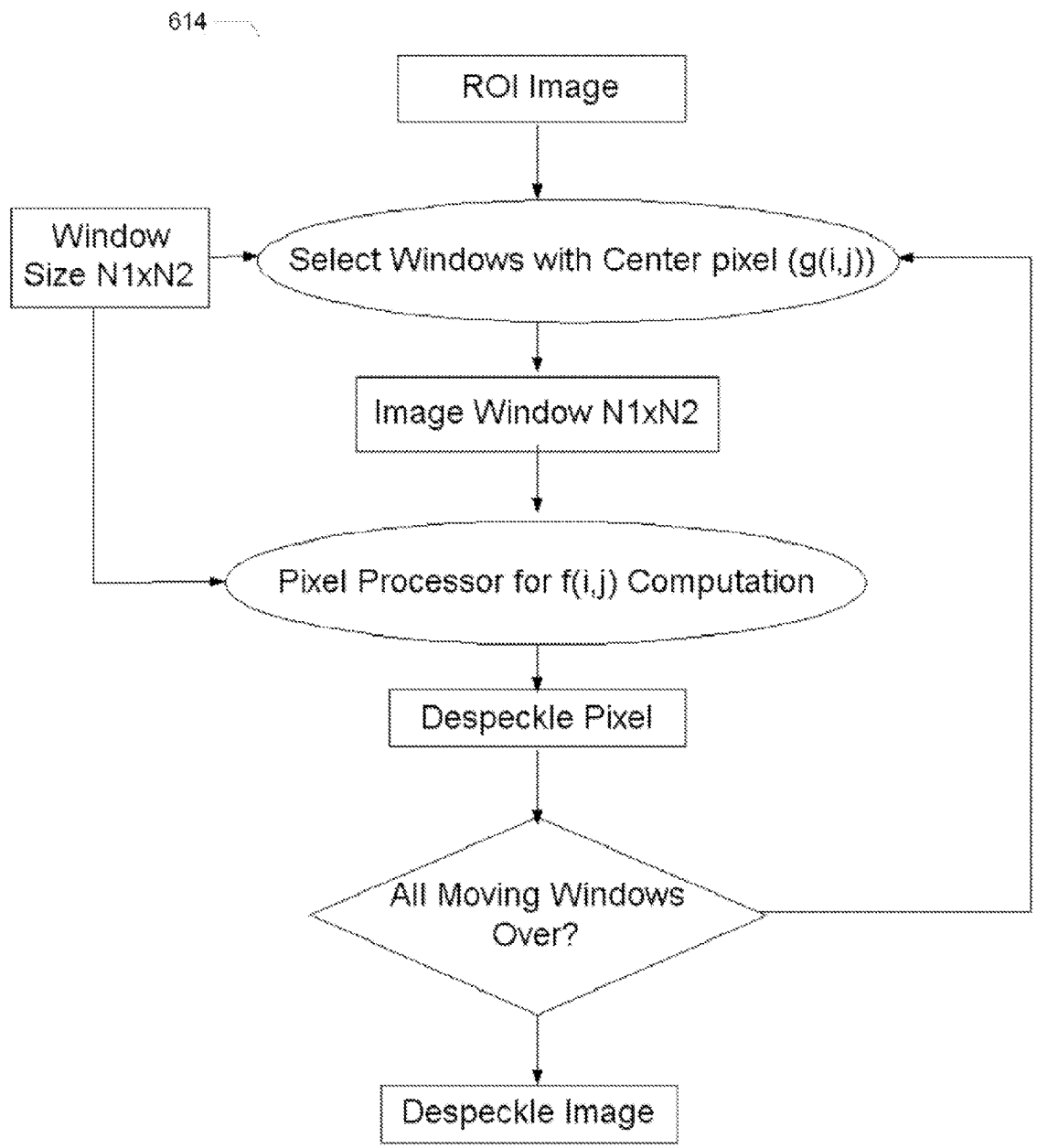
FIG. 9 shows the despeckle processor, which can remove the speckles in the ultrasound region of interest. A moving window method is used for generating the de-speckle filtering process.
Figure 10:
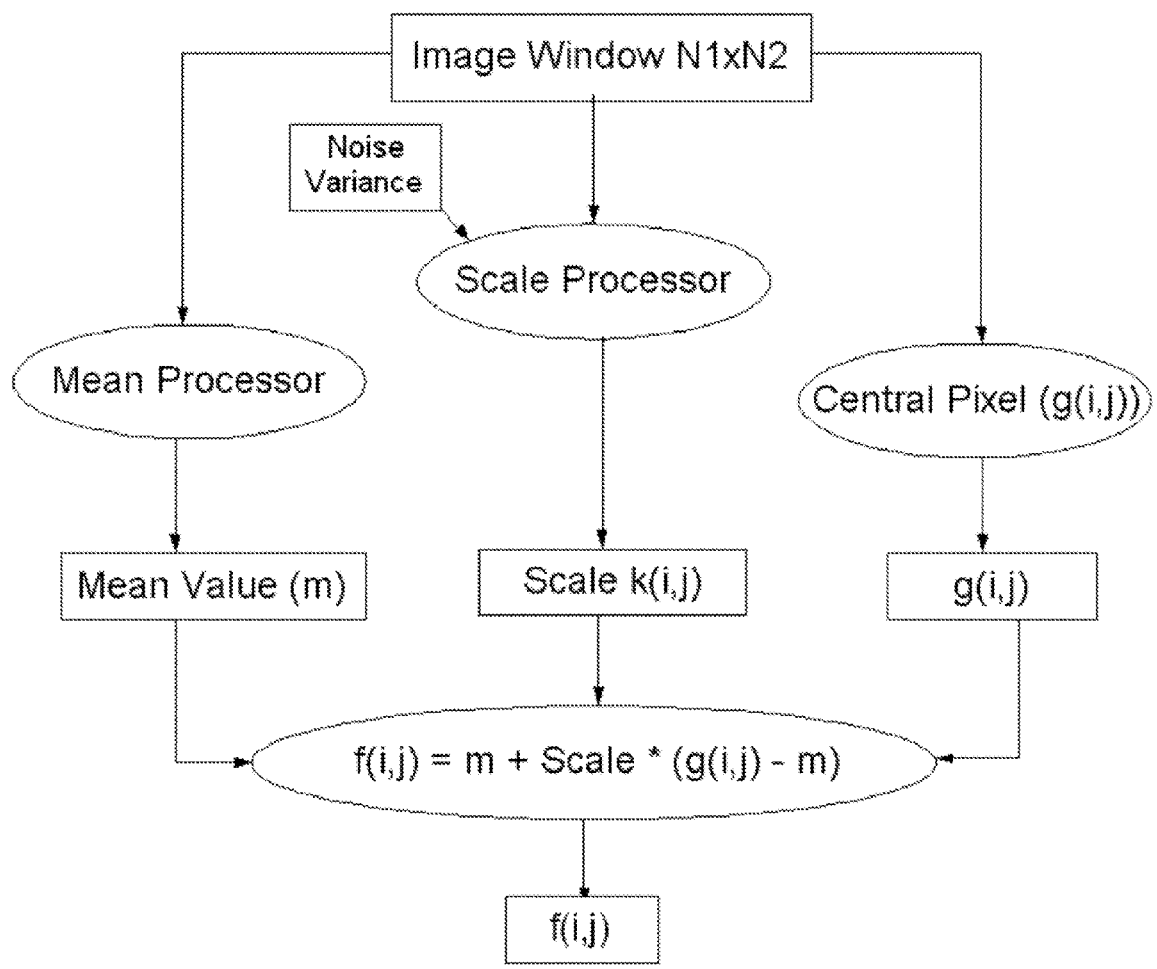
FIG. 10 shows the process for computing the de-speckle pixel and replacing the original noisy pixel. The process uses the scaling of the original pixel. The noise variance process is being used by the scale processor.
Figure 11:
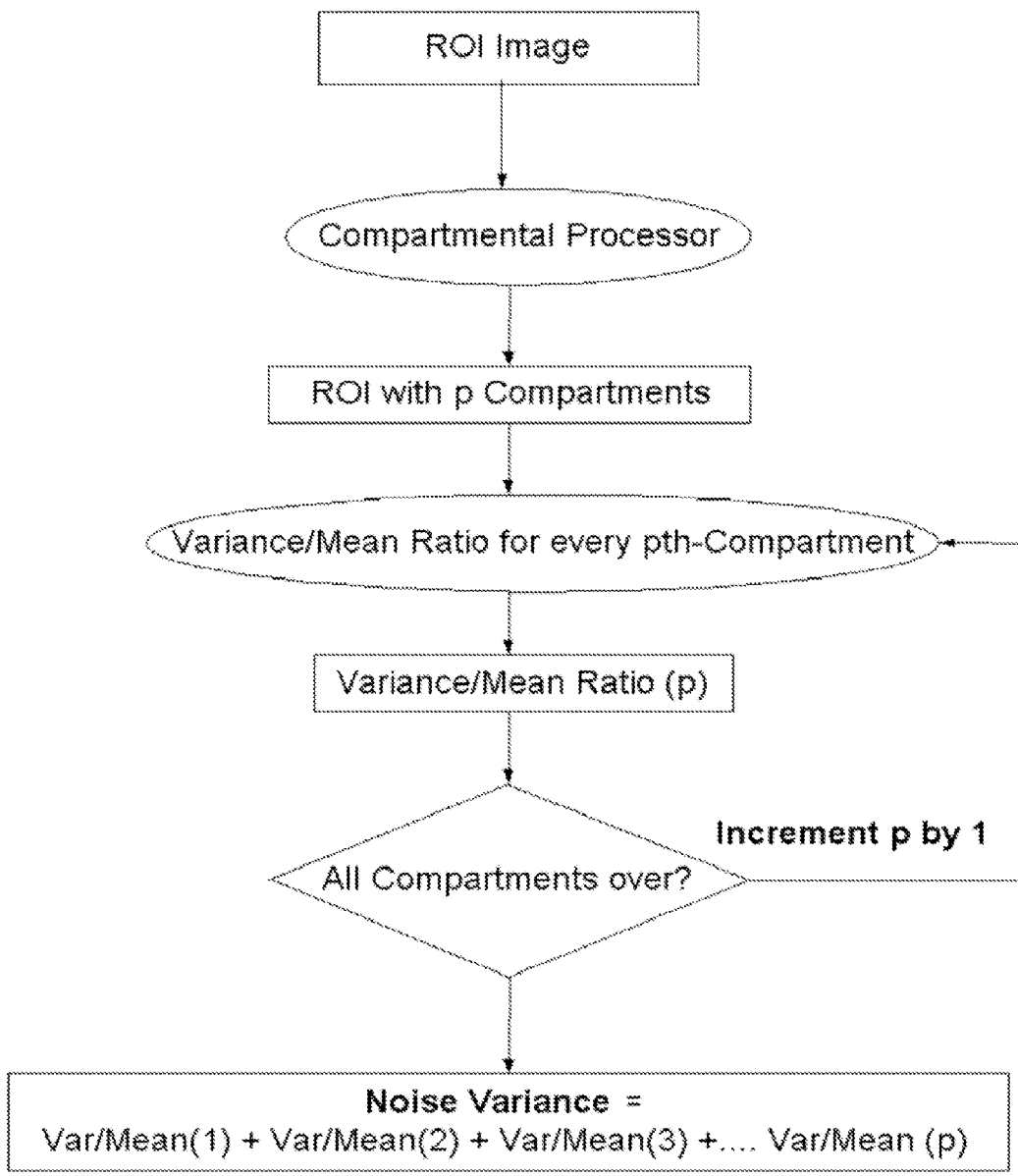
FIG. 11 shows the computation of the noise variance processor. The noise variance is computed by summing the variance to mean ration for all the compartments of the ROI region. The figure shows if there are "p" compartments, then the noise variance is computed by summing the variance to mean ratio of each of the "p" compartments.

FIGS. 9, 10 and 11 deal with the de-speckle filtering component 614; whose output is DDVS (Down sampled Despeckle Vascular Scan). Speckle noise was attenuated by using a first-order statistics filter, which gave the best performance in the specific case of carotid imaging. This filter is defined by the following equation:

$$J_{x,y} = \bar{I} + k_{x,y}(I_{x,y} - \bar{I}) \qquad (1)$$

where, Ix,y is the intensity of the noisy pixel, $\bar{I}$ is the mean intensity of a N×M pixel neighborhood and kx,y is a local statistic measure. The noise-free pixel is indicated by Jx,y. kx,y is mathematically defined $$k_{x,y} = \frac{\sigma_I^2}{\bar{I}^2 \sigma_I^2 + \sigma_n^2},$$

where $\sigma_1^2$ represents the variance of the pixels in the neighborhood, and $\sigma_n^2$ the variance of the noise in the cropped image. An optimal neighborhood size can be 7×7. Note that the despeckle filter is useful in removing the spurious peaks if any during the adventitia identification in subsequent steps.

Figure 12:
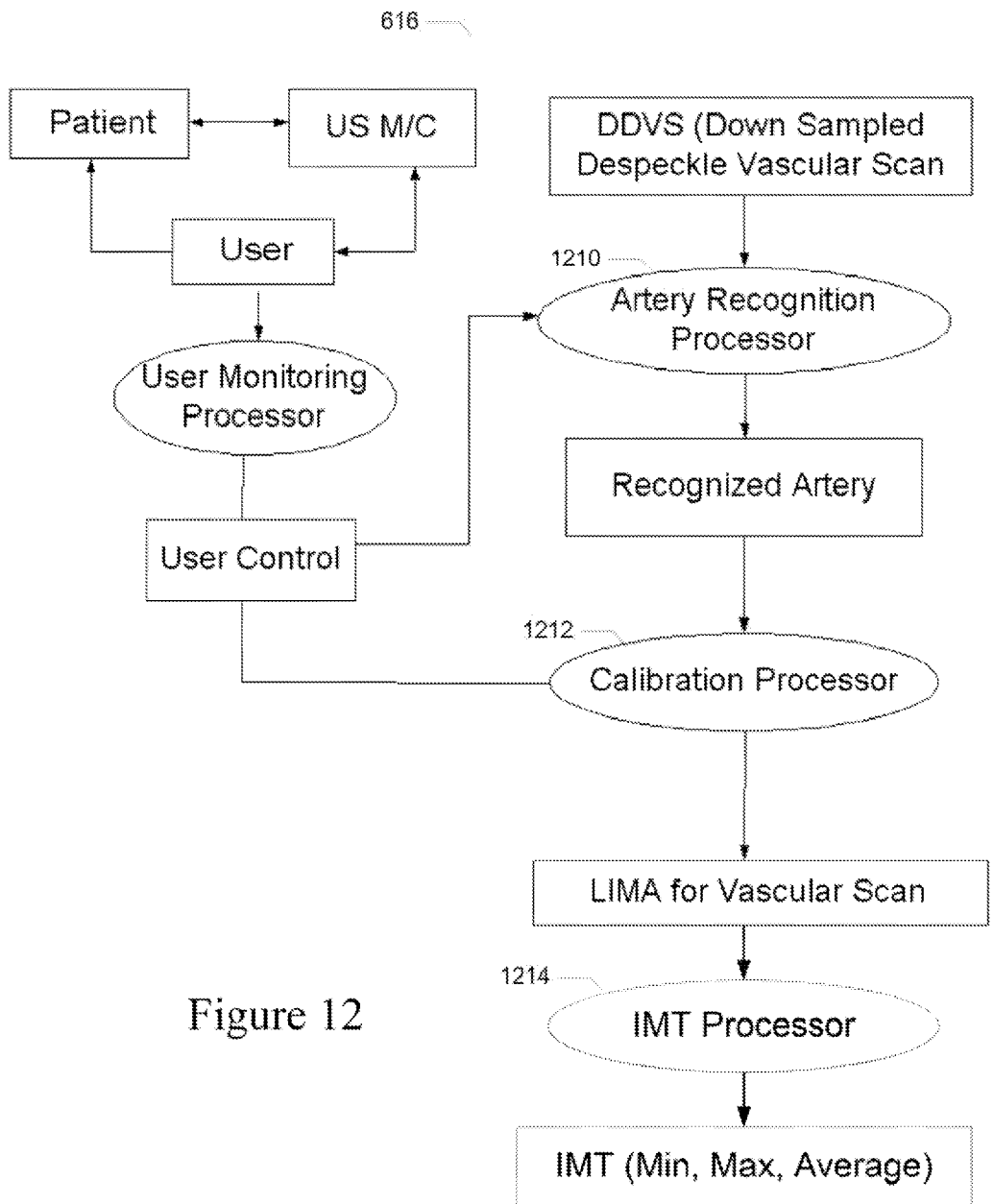
FIG. 12 shows the joint recognition and calibration processor for computing the LIMA borders after the automated recognition process. Calibration phase is definite phase for any LIMA borders to be estimated along with the IMT values.

FIG. 12 shows the last and the final stage is the recognition and calibration system 616 shown in the process called "Completely Automated Recognition and Calibration Processor". While the two stages 1210 and 1212 are cascaded and shown to be different blocks, but it is transparent to the user. This means the software is cascading information from one block to another block without user interaction. The user still has full control and user monitoring processor is fully active and the user can interrupt the system any time.

Figure 13:
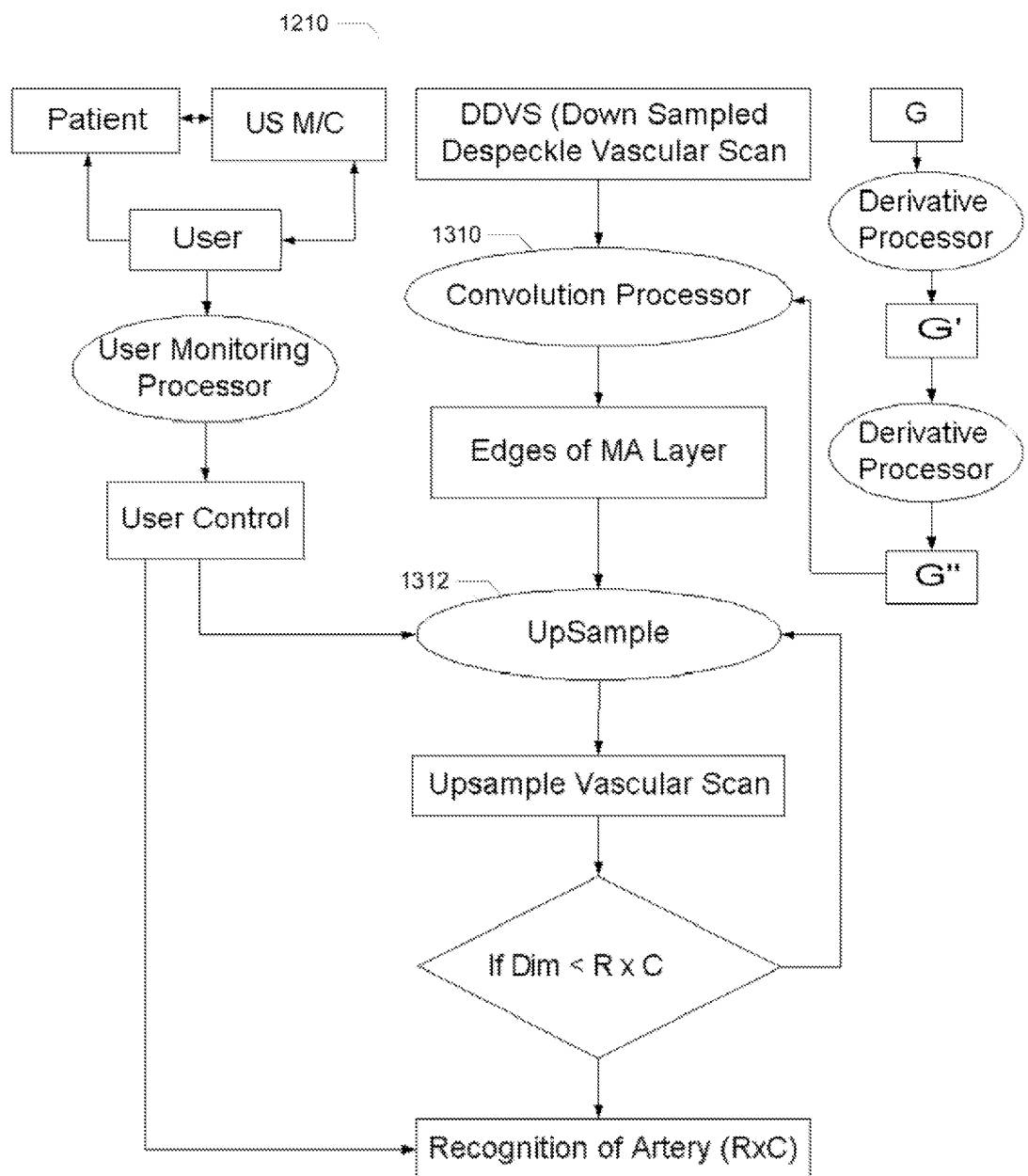
FIGS. 13-14 shows the artery recognition process, where the input image is the down sampled image of the cropped image. These figures also show the edge detection of the MA border by convolution of higher order derivatives of Gaussian kernel with known mean and standard deviation. These figures also show the up-sampling of the MA recognized border for visualization on to the high resolution cropped image.

FIG. 13 shows the Artery Recognition Processor 1210. The Artery Recognition Processor 1210 performs the automated recognition of an artery. The Artery Recognition Processor 1210 of an example embodiment has two stages: (a) convolution and heuristic processor 1310 and (b) up-sample processor 1312.

The convolution processor 1310 is used for convolution of the first order derivative G with the despeckled image. The scale parameter of the Gaussian derivative kernel was taken equal to 8 pixels, i.e. to the expected dimension of the IMT value. In fact, an average IMT value of say 1 mm corresponds to about 16 pixels in the original image scale and, consequently, to 8 pixels in the coarse or down sampled image. The convolution processor 1310 outcome will lead to the clear information for the near and far walls. This information will have two parallel bands corresponding to the far and near vessel walls. These bands will follow the curvature of the vessel walls. If the vessel wall is oriented downwards or upwards or has a bending nature, the bands will follow on both sides of the lumen. These bands have information which corresponds to the maximum intensity saturated to the maximum values of 2 to the power of 8, the highest value. For an 8 bit image, this value will be 255.

The convolution process then allows the heuristics to estimate the Adventitia borders of the far wall or near wall. To automatically trace the profile of the far wall, we used a heuristic search applied to the intensity profile of each column. Starting from the bottom of the image (i.e. from the pixel with the higher row index. The image convention uses (0,0) as top left hand corner of the image), we search for the first white region constituting of at least 6 pixels of width. The deepest point of this region (i.e. the pixel with the higher row index) marked the position of the far adventitia (ADF) layer on that column. The sequence the points resulting from the heuristic search for all the image columns constituted the overall automated far adventitia tracing ADF.

The last stage of the Artery Recognition Processor 1210 is the up-sampling processor 1312 which allows the adventitia tracing ADF to be up-sampled back to the original scale of cropped image. The ADF profile was then up-sampled to the original scale and superimposed over the original cropped image for both visualization and determination of the region of interest for segmentation (or calibration) phase. At this stage, the CA far wall is automatically located in the image frame and automated segmentation is made possible.

This Artery Recognition Processor 1210 (stage I) is an important part of our methodology. The Artery Recognition Processor 1210 consists of a superior architecture based on fine to coarse sampling for vessel wall scale reduction, speckle noise removal, and higher-order Gaussian convolution, and automated recognition of Adventitia. The ability of segmentation or calibration phase (stage II) to be guided by the automated CA wall recognition is in itself a novel contribution. The first-order Gaussian kernel convolution allowed for an optimal detection of the CA walls. This kernel has unitary energy. When such kernel is located in proximity of a neat gray level change, it enhances the transition. Consequently, the most echoic image interfaces are enhanced to white in the filtered image. For this reason, the Artery Recognition Processor 1210 allows for detecting the adventitia layer.

Figure 14:
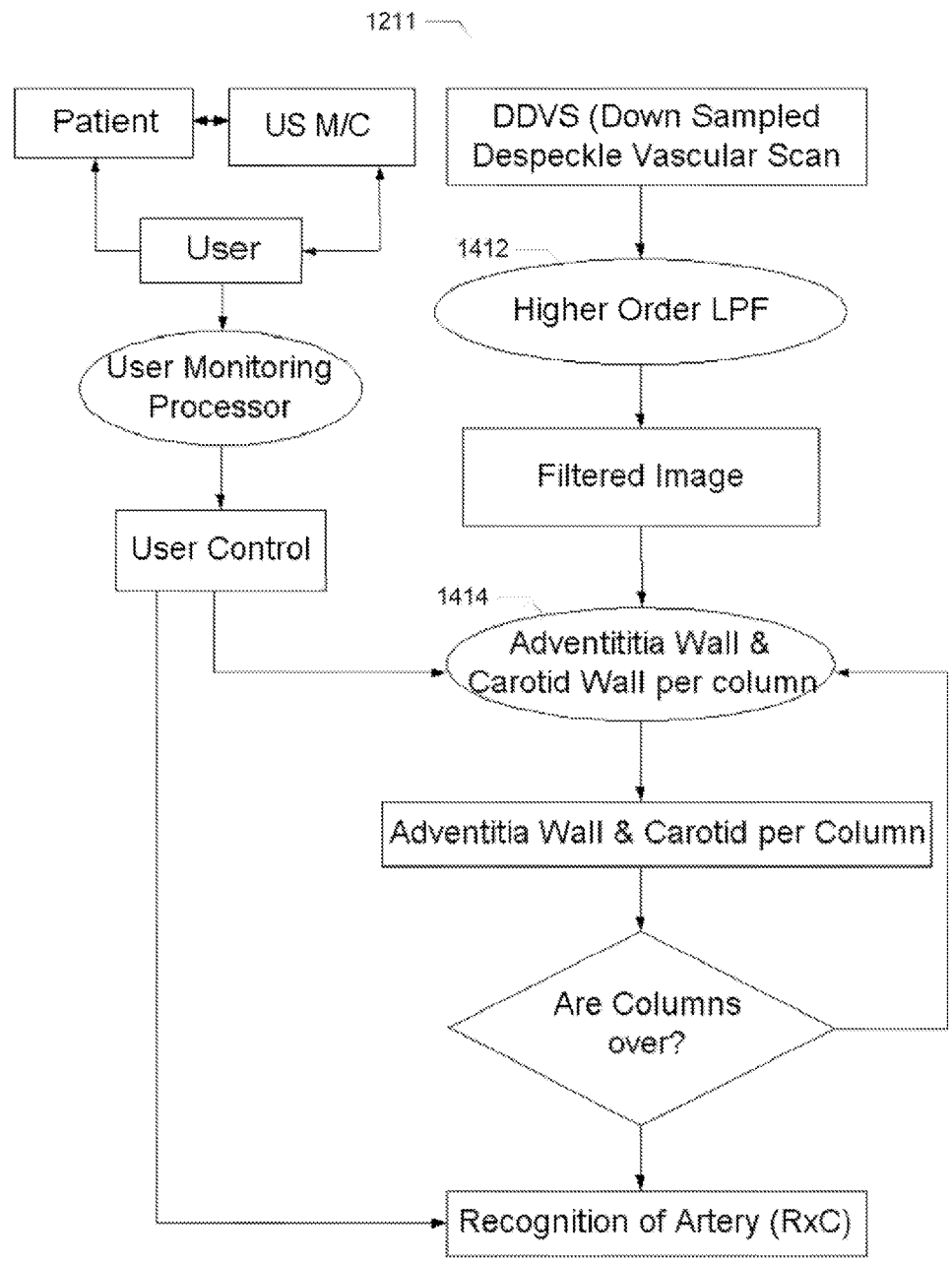

In an alternative embodiment, another combination of Artery Recognition Processor 1210 and a calibration system 1212 can be made; for example, FIG. 14 shows another Artery Recognition Processor 1211 based on the combination of an LPF component 1412 and a Peak Detection system 1414. This Artery Recognition Processor 1211 can also be connected to the calibration system 1212 (stage-II). This Artery Recognition Processor 1211 several advantages to it:

(1) Robustness and Accurate Wall Capture: Artery Recognition Processor 1211 is very robust because the higher order derivative kernels are very good in capturing the vessel walls (see, A Review on MR Vascular Image Processing Algorithms: Acquisition and Pre-filtering: Part I, Suri et al., IEEE TRANSACTIONS ON INFORMATION TECHNOLOGY IN BIOMEDICINE, VOL. 6, NO. 4, pp. 324-337, December 2002; and A Review on MR Vascular Image Processing: Skeleton Versus Nonskeleton Approaches: Part II, Suri et al., *IEEE TRANSACTIONS ON INFORMATION TECHNOLOGY IN BIOMEDICINE, VOL.* 6, NO. 4, December 2002).

(2) Faster than the conventional processing: Since the recognition is strategized at coarse level down sampled twice from its original size of the image, it is therefore processing ¼$^{th}$ the number of pixels for automated recognition of the media layer. This improves the speed of the system.

(3) Independent of Orientation of the vascular scan: Another major advantage to the system is that these Gaussian kernels are independent of the orientation of the blood vessels in the image. Since the ultrasound vascular scans do not always have the vessel orientation horizontal with respect bottom edge of the image, manual methods can pose a further challenge towards the region of interest estimation.

(4) Guiding Method for the Calibration System: Since the recognition is followed by the calibration process, the calibration system becomes very robust since the calibration processing is done in the region of interest determined by the automated recognition system. Thus the calibration system adds the value determined by the automated recognition system for vascular ultrasound such as IMT measurement for carotid, femoral, aortic and brachial. Such a combination where the calibration system is guided by the automated recognition system helps in mass processing of huge database processing.

(5) Running the Mass IMT system for Clinical Analysis: Since the recognition is automated followed by the calibration system, the largest value such a system would deliver will be in its real time use for analysis of IMT measurement on a large databases. Running clinical databases on still images would be even more beneficial because such a system would be completely automated in terms of recognition and IMT measurement.

(6) Applications: Since the ultrasound probes use almost the same frequency of operation for scanning the vascular arteries such as carotid, femoral, brachial and aortic, it is thus possible to use such a system for these blood vessels.

Figure 15:
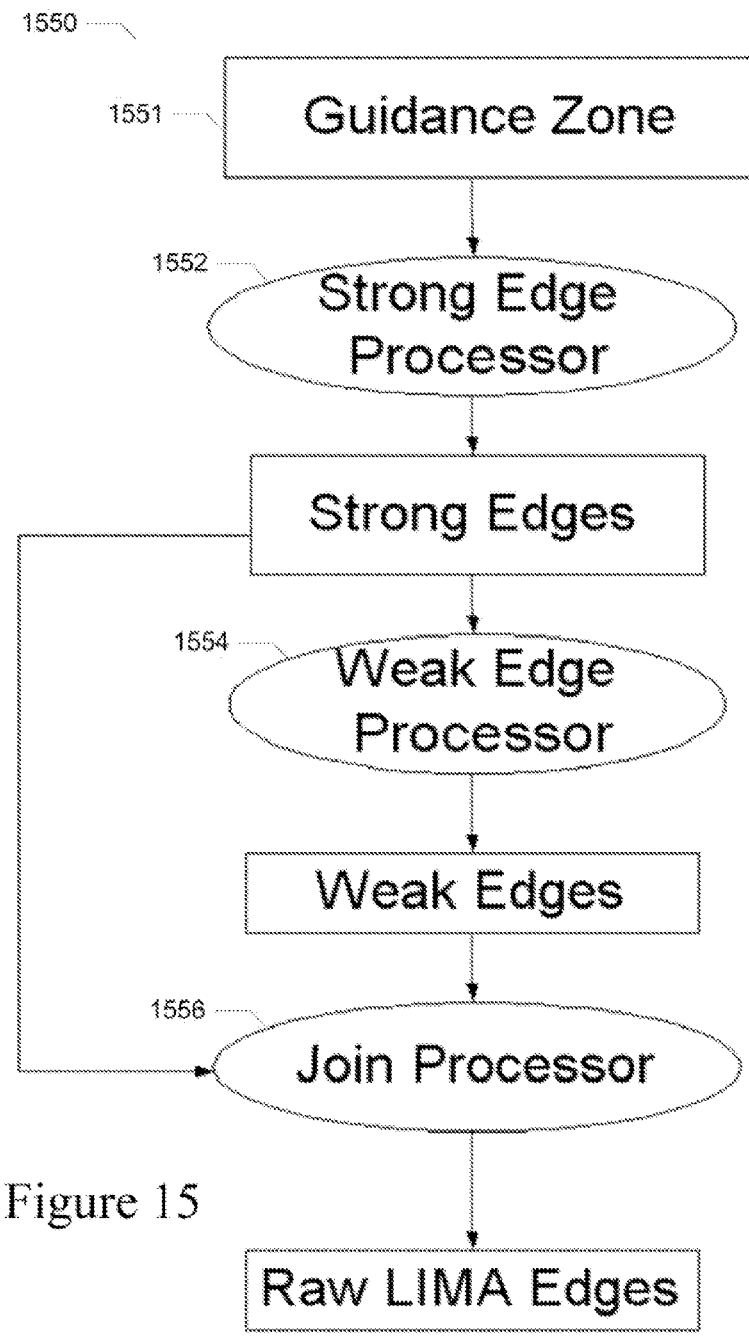
FIG. 15 is the Edge Flow Processor of an example embodiment. The Edge Flow Processor of an example embodiment consists of a strong edge processor, weak edge processor and join processor.

FIG. 15 shows the calibration processor or segmentation processor 1550 (also denoted herein as the Edge Flow Processor) of an example embodiment. It is also called the stage-II process. The calibration processor 1550 includes a Guidance Zone Processor 1551, which consists of estimating the guidance zone in which the segmentation is performed. The Guidance Zone image is passed to the Strong Edge Processor 1552. This estimates the strong MA and strong LI edges. The input to the Weak Edge Processor 1554 receives the strong MA and LI edges and computes the missing or weak edges. Finally, the join processor 1556 receives the strong and weak edges and completes the MA and LI borders.

The Guidance Zone is built around the adventitia tracing ADF. The Guidance Zone is a region-of-interest (ROI) around the automatically traced ADF profile, so called the domain region in which segmentation will run. The ROI is designed such that it has the same width as of the ADF curve. This will allow the creation of the largest possible ROI, according the detected length of the adventitia layer. The height has to be equal to 30 pixels (1.8 mm for images with 16.67 pixels/mm of density, and 1.875 mm for images with 16 pixels/mm of density). For each point of the ADF profile we considered as upper limit of the ROI the pixel with a row index of 30 pixels lower, towards the upper edge of the cropped image. Substantially, the bottom limit of the ROI was the ADF curve while the upper limit was ADF shifted by 30 pixels.

Stage H

Edge Flow Magnitude and Edge Flow Direction:

FIG. 15 illustrates the Edge Flow Processor 1550 of an example embodiment. The Edge Flow Processor 1550 of an example embodiment includes a strong edge processor 1552, weak edge processor 1554, and join processor 1556.

Strong edge processor 1552 is used for computing the strong MA and LI edge based on the computation of the edge flow. The method described herein facilitates the integration of different image attributes into a single framework for boundary detection and is based on the construction of an edge flow vector defined as:

$$F(s,\theta)=F[E(s,\theta),P(s,\theta),P(s,\theta+\pi)] \quad (2)$$

where:
$E(s,\theta)$ is the edge energy at location s along the orientation $\theta$;
$P(s,\theta)$ represents the probability of finding the image boundary if the corresponding edge flow "flows" in the direction $\theta$;
$P(s,\theta+\pi)$ represents the probability of finding the image boundary if the edge flow "flows" backwards, i.e., in the direction $\theta+\pi$.

The final single edge flow vector can be thought of as the combination of edge flows obtained from different types of image attributes. The image attributes that we considered are intensity and texture. In order to calculate the edge energy and the probabilities of forward and backward edge flow direction, a few definitions must first be clarified, specifically the first derivative of Gaussian (GD) and the difference of offset Gaussian (DOOG).

Considering the Gaussian kernel $G_\sigma(x,y)$, where $\sigma$ represents the standard deviation, the first derivative of the Gaussian along the x-axis is given by:

$$GD_\sigma(x,y) = -\left(\frac{x}{\sigma^2}\right)g_\sigma(x,y) \quad (3)$$

and the difference of offset Gaussian (DOOG) along the x-axis is defined as:

$$DOOG_\sigma(x,y)=G_\sigma(x,y)-G_\sigma(x+d,y) \quad (4)$$

where d is the offset between centers of two Gaussian kernels and is chosen proportional to $\sigma$. This parameter is significant in the calculation of the probabilities of forward and backward edge flow, as it is used to estimate the probability of finding the nearest boundary in each of these directions. By rotating these two functions, we can generate a family of previous functions along different orientations $\theta$ and they can be denoted as $G_{\sigma,\theta}(x,y)$ and $DOOG_{\sigma,\theta}(x,y)$, respectively:

$$GD_{\sigma,\theta}(x,y)=GD_\sigma(x',y') \quad (5)$$

$$DOOG_{\sigma,\theta}(x,y)=DOOG_\sigma(x',y') \quad (6)$$

where: $x'=x\cos\theta+y\sin\theta$, and $y'=x\sin\theta+y\cos\theta$

Intensity Edge Flow:

Considering the original image $I(x,y)$ at a certain scale $\sigma$, $I_\sigma(x,y)$ is obtained by smoothing the original image with a Gaussian kernel $G_\sigma(x,y)$. The edge flow energy $E(s,\theta)$ at scale $\sigma$, defined to be the magnitude of the gradient of the smoothed image $I_\sigma(x,y)$ along the orientation $\theta$, can be computed as:

$$E(s,\theta)=|I(x,y)*GD_{\sigma,\theta}| \quad (7)$$

where s is the location (x,y). This energy indicates the strength of the intensity changes. The scale parameter is very important in that it controls both the edge energy computation and the local flow direction estimation so that only edges larger than the specified scale are detected.

To compute $P(s,\theta)$, two possible flow directions ($\theta$ and $\theta+\pi$) are considered for each of the edge energies along the orientation $\theta$ at location s. The prediction error toward the surrounding neighbors in these two directions can be computed as:

$$Error(s,\theta)=|I_\sigma(x+d\cos\theta,y+d\sin\theta)-I_\sigma(x,y)|=|I(x,y)*DOOG_{\sigma,\theta}(x,y)| \quad (8)$$

where d is the distance of the prediction and it should be proportional to the scale at which the image is being analyzed.

The probabilities of edge flow direction are then assigned in proportion to their corresponding prediction errors, due to the fact that a large prediction error in a certain direction implies a higher probability of locating a boundary in that direction:

$$P(s, \theta) = \frac{\text{Error}(s, \theta)}{\text{Error}(s, \theta) + \text{Error}(s, \theta + \pi)} \quad (9)$$

Texture Edge Flow:

Texture features are extracted from the image based on Gabor decomposition. This is done basically by decomposing the image into multiple oriented spatial frequency channels, and then the channel envelopes (amplitude and phase) and used to form the feature maps.

Given the scale σ, two center frequencies of the Gabor filters (the lowest and the highest) are defined and based on the range of these center frequencies, an appropriate number of Gabor filters $g_i(x,y)$ is generated. The complex Gabor filtered images are defined as:

$$O_i(x,y) = I * g_i(x,y) = m_i(x,y) \exp[\Phi_i(x,y)] \quad (10)$$

where $1 \leq i \leq N$, N is the total number of filters and i is the sub band, $m_i(x,y)$ is the magnitude, and $\Phi_i(x,y)$ is the phase. A texture feature vector $\Psi(x,y)$ can then be formed by taking the amplitude of the filtered output across different filters at the same location (x,y):

$$\Psi(x,y) = [m_1(x,y), m_2(x,y), \ldots, m_N(x,y)] \quad (11)$$

The change in local texture information can be found using the texture features, thus defining the texture edge energy:

$$E(s, \theta) = \sum_{1 \leq i \leq N} |m_i(x, y) * GD_{\sigma,\theta}(x, y)| \cdot w_i \quad (12)$$

where $$w_i = \frac{1}{\|\alpha_i\|}$$

and $\|\alpha_i\|$ is the total energy of the sub band i.

The direction of the texture edge flow can be estimated similarly to the intensity edge flow, using the prediction error:

$$\text{Error}(s, \theta) = \sum_{1 \leq i \leq N} |m_i(x, y) * DOOG_{\sigma,\theta}(x, y)| \cdot w_i \quad (13)$$

and the probabilities $P(s,\theta)$ of the flow direction can be estimated using the same method as was used for the intensity edge flow.

Combining Edge Flow from Intensity and Texture:

For general-purpose boundary detection, the edge flows obtained from the two different types of image attributes can be combined:

$$E(s, \theta) = \sum_{a \in A} E_s(s, \theta) \cdot w(a), \quad \sum_{a \in A} w(a) = 1 \quad (14)$$

$$P(s, \theta) = \sum_{a \in A} P_a(s, \theta) \cdot w(a) \quad (15)$$

where $E_u(s,\theta)$ and $P_a(s,\theta)$ represent the energy and probability of the edge flow computed from the image attributes a (in this case, it is intensity and texture). w(a) is the weighting coefficient among various types of image attributes. To identify the best direction for searching for the nearest boundary, we are supposed to have edge flows $\{F(s,\theta)|_{0 \leq \theta \leq \pi}\}$ and identify a continuous range of flow directions which maximizes the sum of probabilities in that half plane:

$$\Theta(s) = \arg\max_\theta \left\{ \sum_{\theta \leq \theta^* \leq \theta + \pi} P(s, \theta) \right\} \quad (16)$$

The vector sum of the edge flows with their directions in the identified range is what defines the final resulting edge flow and is given by:

$$\vec{F}(s) = \sum_{\Theta(s) \leq \theta \leq \Theta(s) + \pi} E(s, \theta) \cdot \exp(j\theta) \quad (17)$$

where $\vec{F}(s)$ is a complex number whose magnitude represents the resulting edge energy and whose angle represents the flow direction.

Flow Propagation and Boundary Detection

Once the edge flow $\vec{F}(s)$ of an image is computed, boundary detection can be performed by iteratively propagating the edge flow and identifying the locations where two opposite direction of flows encounter each other. The local edge flow is then transmitted to its neighbor in the direction of flow if the neighbor also has a similar flow direction. The steps which describe this iterative process are as follows:

STEP 1: Set n=0 and $\vec{F}_0(S) = \vec{F}(s)$

STEP 2: Set the initial edge flow $\vec{F}_{n+1}(s)$ at time n+1 to zero

STEP 3: At each image location s=(x,y), identify the neighbour s'=(x',y') which is in the direction of edge flow $\vec{F}_n(S)$ STEP 4: Propagate the edge flow if $\vec{F}_n(s') \cdot P(s) > 0$ $$\vec{F}_{n+1}(s') = \vec{F}_{n+1}(s') + \vec{F}_n(s);$$

otherwise, $$\vec{F}_{n+1}(s) = \vec{F}_{n+1}(s) + \vec{F}_n(s)$$

STEP 5: If nothing has been changed, stop the iteration. Otherwise, set n=n+1 and go to step 2.

Figure 21:
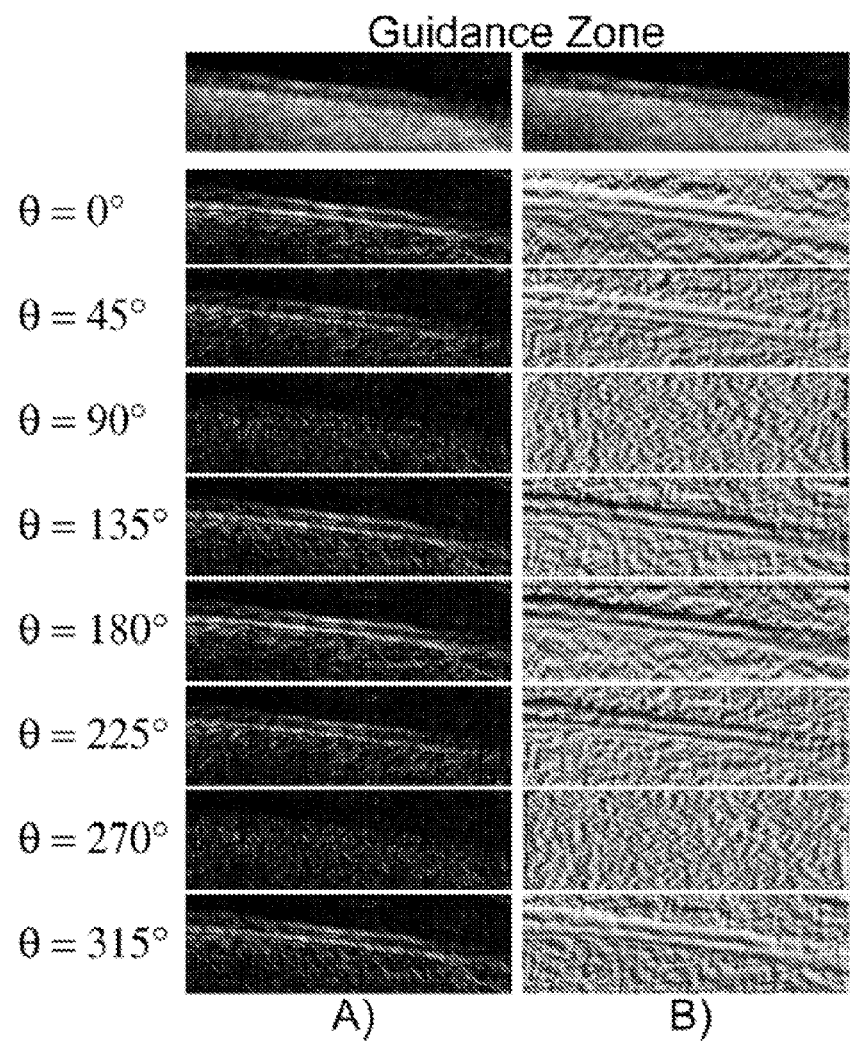
FIG. 21 shows the edge flow intensity and probability and the Guidance Zone.

The image boundaries can then be detected once the edge flow propagation reaches a stable set by identifying the locations which have non-zero edge flow coming from two opposing directions. For all of the images, we considered eight different orientations, starting from 0° and going to 315° with equal degree intervals in between. FIG. 21 shows the total energy of the edge flow $E(s,\theta)$ obtained for the various orientations and their corresponding total probabilities of the edge flow $P(s,\theta)$. FIG. 22(A) shows the energy flow edge flow $E(s,\theta)$ applied to nine samples. FIG. 22(B) shows the corresponding total probabilities of the edge flow $P(s,\theta)$.

Once the image boundaries are detected, the final image is generated by performing region closing on it to limit the number of disjoint boundaries by searching for the nearest boundary element, which is within the specified search neighborhood at the unconnected ends of the contour. If a boundary element is found, a smooth boundary segment is generated to connect the open contour to another boundary element. The neighborhood search size is taken to be proportional to the length of the contour itself.

This approach of edge detection has some very salient features, including the fact that it uses a predictive coding model for identifying and integrating the different types of image boundaries, the boundary detection is based on flow field propagation and it has very few "free" parameters that control the segmentation. Because of this, very little parameter tuning or selection is needed and the sole parameter that controls the segmentation is the preferred image scale.

FIG. 23 shows an example of an output image from the Edge Flow process. FIG. 23 shows this output binary image overlaid on the original image in red, once converted back to the original image size.

As FIG. 23 clearly shows, the edge flow process over-segments in many different points, due partly to the fact that the image was cropped to contain the entire Guidance Zone Mask and therefore may contain sections of the image that are found below the ADF profile. Also, while part of the MA and LI edge estimation may be done using the edge flow process, the segmentation cannot yet be considered complete as there are still some missing MA and LI edges and the edges found must be classified as either belonging to the MA profile or the LI profile. This refinement and classification process is done using a strong dependency on the edges found by the edge flow process and via labeling and connectivity.

MA weak/missing edge estimation using MA strong edge dependency via labeling and connectivity and complete MA estimation: In this step all the edge objects in the output image that are not included in the Guidance Zone are eliminated, thus discarding many of the over-segmented edge objects found below the ADF profile. An edge object is defined as a connected component in the binary image.

Small Edge Objects:

Secondly, since there can still be small unwanted edge objects around the interested area, small edge objects are defined as those which have an area ratio below a certain limit $\phi$ and are subsequently removed from the image. The area ratio is defined by the following equation:

$$AreaRatio = \frac{Area_{EdgeObject}}{Area_{AllEdgeObjects}} \leq \phi \Rightarrow SmallEdgeObject \quad (18)$$

MA Estimation:

Our experimental data showed that, when $\phi=0.1$ we are successfully able to discard the small edge objects. The MA segment is then first initialized as being the edge object with the highest pixel row index (i.e., the lowest edge object in the image) and its unconnected end points are found as the right top and left top pixels of the edge object (RTMA and LTMA, respectively). The remaining edge objects are then sorted by their mean pixel row index value so as to examine the edge objects starting from those which are lowest in the image and working upwards. The edge objects are then classified by following these steps:

1. Find the unconnected end points of the i-th edge object as the right top and left top pixels of the examined edge object ($RT_i$ and $LT_i$ respectively).
2. Determine the correct unconnected end point pair (either $LT_{MA}$ and $RT_i$ or $LT_i$ and $RT_{MA}$) as the pair which yields a lesser column difference in absolute value:

$$\left| LT_{x_{MA}} - RT_{x_{i_{MA}}} \right| \quad (19)$$

Figure 24A:
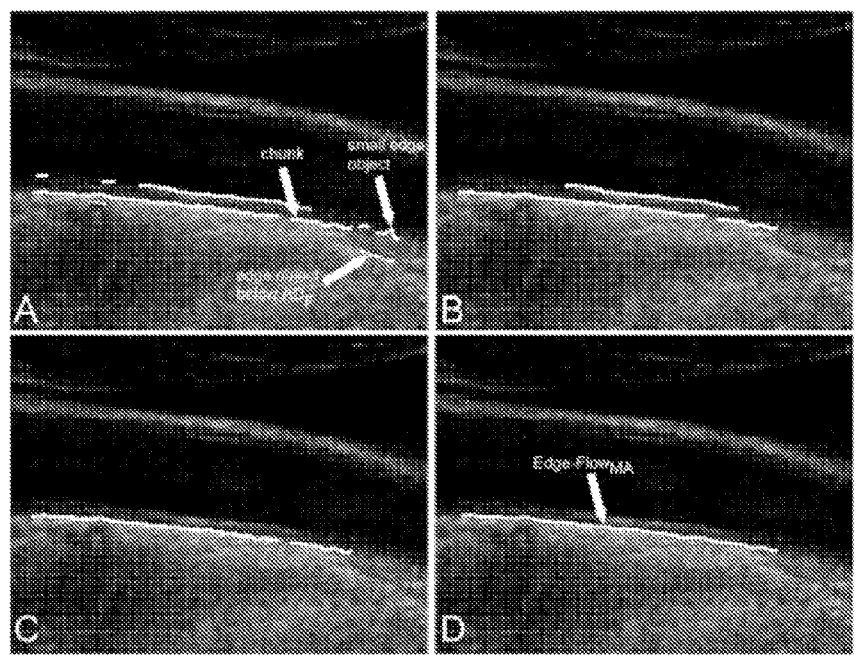

3. Calculate the respective row distance in absolute value ($|LT_y-RT_y|$) and column distance ($LT_x-RT_x$) between the correct unconnected end point pair found and determine that the examined edge object can be classified as being part of the MA segment if the following two conditions are met:

$$|LT_y-RT_y| \leq \phi \quad (20)$$

$$LT_x-RT_x > 0 \quad (21)$$

where $\phi$ is the maximum row distance acceptable, which we took to be equal to 15. The condition on the column distance is needed to ensure that the edge object considered does not overlap the already existing MA segment, while the condition on the row distance is necessary so as to avoid including edges that are too far above the existing MA segment.
4. Find new unconnected end points of the MA segment.
5. Repeat steps 1-4 until all edge objects have been examined. FIG. 24A shows the edge objects that were classified as being part of the MA segment overlaid in red on the original image.

Once all of the edge objects have been examined, those which are classified as being part of the MA segment are then connected together and regulated using a B-spline to produce the final MA profile. FIG. 24A shows an example of a result of this operation. FIG. 24B shows the results after the MA refinement on the nine sample images.

LI Weak/Missing Edge Estimation Using LI Strong Edge Dependency and Complete MA Edge Dependency:

The LI missing edge estimation is completely dependent on the MA profile which is determined in pervious stage. In fact, the MA profile is used to create a guidance zone starting from the profile and extending it upwards 50 pixels (FIG. 25). This is used to find solely the edge objects from the image output of the edge flow process that can be found above (lower row value) the MA profile and that have at least some common support with it.

Referring to FIG. 25, once this step is done, the following steps are necessary for each of these "i" edge objects:
1. Find the common support between the MA profile and the i-th edge object and cut the MA profile to the common support ($MAcut_i$).
2. Create a mask starting from $MAcut_i$ and extending it upwards 10 pixels and calculate the mean ($IM_{mean_{GT}}$) and standard deviation ($IM_{std_{GT}}$) of the pixel values found in the mask (FIG. 25).
3. Create a second mask starting from $MAcut_i$ and extending it up to the i-th edge object (FIG. 25). For each pixel found in this mask, determine if it can be defined as an acceptable pixel based on the following equation:

$$|PixelValue - IM_{mean_{GT}}| < IM_{std_{GT}} \Rightarrow AcceptablePixel \quad (22)$$

and determine an $IM_{ratio}$ as the ratio between the number of acceptable pixels found and the total number of pixels considered (see FIG. 25).
4. Calculate the row distance between the left unconnected end point of the i-th edge object and the first point of $MAcut_i$ ($LT_{y_i}-LT_{y_{MA}}$) and the row distance between the right unconnected end point of the i-th edge object and the last point of $MAcut_i$ ($RT_{y_i}-RT_{y_{MA}}$).

5. Determine that the edge object can be classified as being part of the LI segment if the following two conditions are met:

$$IM_{ratio_i} > 0.4 \quad (23)$$

$$\text{mean}(LT_{y_i} - LT_{y_{MA}}, RT_{y_i} - RT_{y_{MA}}) > 5 \quad (24)$$

The first condition is important in that it avoids classifying an edge object which is found in the lumen since the pixel values in the lumen are considerably lower than $IM_{mean_{GT}}$ and those pixels would therefore not be classified as an acceptable pixel, lowering by a good deal the calculated $IM_{ratio}$. The second condition is necessary so as to not include over-segmented edge objects, which are located too close to the MA profile (i.e., in between the MA and LI profiles.)

6. Repeat steps 1-5 until all edge objects are examined. FIG. 25 shows the edge objects that were classified as being part of the LI segment overlaid in red on the original image.

Once all of the edge objects are examined, those found to be part of the LI segment (good edge objects) must be tested to see if the distance between two adjacent edges objects is too vast. This is to avoid connecting two edge objects which are too far from each other, which could have a negative effect on the outcome of the final LI profile. FIG. 26 shows the LI refinement process on the nine sample images.

To do this, the good edge objects are considered by adjacent pairs. The Euclidean distance between the two closest unconnected end points of the pair is calculated and if this distance exceeds a certain limit, the good edge objects are classified as belonging to two different LI segments. If the distance calculated is less than the defined limit, then the pair is classified as belonging to the same LI segment. Once all good edge objects have been examined, the final LI segment is determined by those that are part of the longest LI segment found (FIG. 26). The edge objects that are part of the final LI segment are then connected together and regulated using a B-spline to produce the final LI profile (FIG. 27).

Performance Metric

Figure 28A:
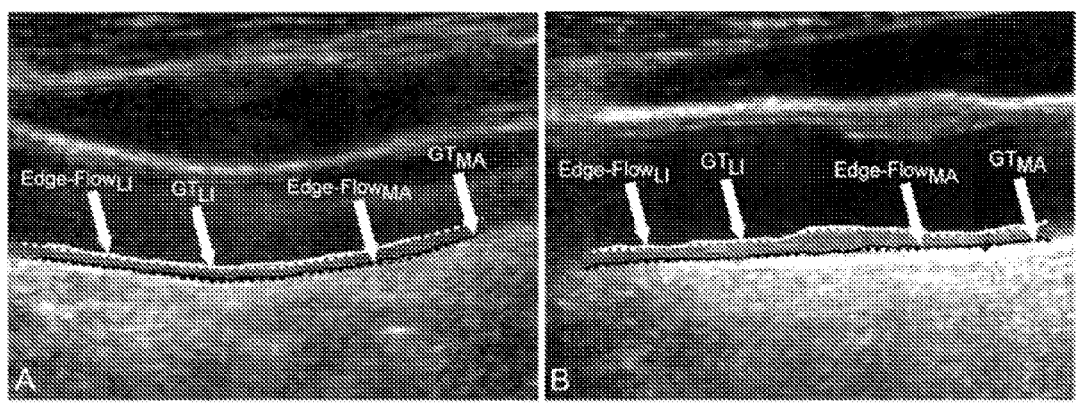

Referring to FIGS. 28A and 28B, the method of an example embodiment was tested on a multi-institutional database consisting of 300 longitudinal B-mode ultrasound images of the CA. We then had three expert operators independently and manually trace the LI and MA profiles in all of the images. Ground truth (GT) was then considered as the average profile of the human tracings. The operators manually segmented the images by using a MATLAB interface we previously developed. The manual profiles were interpolated by a B-spline and averaged. The averaged profile was considered as ground-truth (GT). FIG. 28A shows the LIMA borders. FIG. 28B shows the LIMA borders along with the Ground Truth borders.

Our performance evaluation method consisted in two different strategies:
(i) To assess the performance of the automated tracing of the far adventitial border;
(ii) Overall system distance of the LI/MA traced profiles from GT and of the IMT measurement bias.

Concerning (i), we calculated the Hausdorff distance (HD) between the ADF profile and the LIGT profile and then between the ADF profile and the MAGT profile for each image, to find the LI and MA error between ADF and GT ($\epsilon_{ADF\text{-}GT}^{LI}$ and $\epsilon_{ADF\text{-}GT}^{MA}$, respectively). The HD between two boundaries is a measure of the farthest distance that must be covered moving from a given point on one boundary and travelling to the other boundary. So first of all, given two boundaries B1 and B2, the Euclidean distances of each vertex of B1 from the vertices of B2 must be calculated. For every vertex of B1, the minimum Euclidean distance is kept. Then once all B1 vertexes have been examined, the maximum distance between all of these minimum distances is kept and we can indicate it with d12. Likewise, we can calculate the Euclidean distances of each vertex of B2 from the vertices of B1 and find d21. The HD can then be mathematically defined as:

$$HD = \max\{d_{12}, d_{21}\} \quad (25)$$

This assessment helps give a general idea of how far the ADF tracing is from the actual distal wall LI and MA borders. Since this distance measure is sensitive to the longest distance from the points of one boundary to the points of the other, we cut the computed profiles to the same support of GT, rendering the HD unbiased by points that could perhaps be located out of the GT support.

Regarding the second point (ii), to assess the performance of the automatic tracings of the LI and MA profiles, we calculated the polyline distance (PD) as proposed by Suri et al in 2000[15].

Considering two boundaries B1 and B2, we can define the distance d(v,s) between a vertex v and a segment s. Let's consider the vertex $v = (x_0, y_0)$ on the boundary B1 and the segment s formed by the endpoints $v_1 = (x_1, y_1)$ and $v_1 = (x_2, y_2)$ of B2. The PD d(v,s) can then be defined as:

$$d(v, s) = \begin{cases} d_\perp & 0 \le \lambda \le 1 \\ \min\{d_1, d_2\} & \lambda < 0, \lambda > 1 \end{cases} \quad (29)$$

where $$d_1 = \sqrt{(x_0 - x_1)^2 + (y_0 - y_1)^2} \quad (30)$$

$$d_2 = \sqrt{(x_0 - x_2)^2 + (y_0 - y_2)^2} \quad (31)$$

$$\lambda = \frac{(y_2 - y_1)(y_0 - y_1) + (x_2 - x_1)(x_0 - x_1)}{(x_2 - x_1)^2 + (y_2 - y_1)^2} \quad (32)$$

$$d_\perp = \frac{(y_2 - y_1)(x_1 - x_0) + (x_2 - x_1)(y_0 - y_1)}{\sqrt{(x_2 - x_1)^2 + (y_2 - y_1)^2}} \quad (33)$$

being $d_1$ and $d_2$ the Euclidean distances between the vertex v and the endpoints of segment s, $\lambda$ the distance along the vector of the segment s, and $d_\perp$ the perpendicular distance between v and s. The polyline distance from vertex v to the boundary B2 can be defined as $$d(v, B_2) = \min_{s \in B_2} \{d(v, s)\}.$$

The distance between the vertexes of B1 to the segments of B2 is defined as the sum of the distances from the vertexes of B1 to the closest segment of B2:

$$d(B_1, B_2) = \sum_{v \in B_1} d(v, B_2) \quad (34)$$

Similarly, the distance between the vertices of B2 to the closest segment of B1 ($d(B_2, B_1)$) can be calculated by simply swapping the two boundaries. Finally, the polyline distance between two boundaries is defined as:

$$PD = \frac{d(B_1, B_2) + d(B_2, B_1)}{(\# \ vertices_{B_1} + \# \ vertices_{B_2})} \quad (35)$$

Using the polyline distance metric, one can then compute the IMT using edge flow method and compare that with the IMT using the GT LIMA borders:

$$IMT_{CADLES-EF} = PD(LI_{CADLES-EF}, MA_{CADLES-EF}) \quad (36)$$

$$IMT_{GT} = PD(LI_{GT}, MA_{GT}) \quad (37)$$

$$\epsilon_{CABLES-EF}^{IMT} = IMT_{CADLES-EF} - IMT_{GT} \quad (38)$$

The PD measures the distance between each vertex of a boundary and the segments of the other boundary.

This assessment helps evaluate the performance of the IMT using Edge Flow and the error is purposefully calculated without an absolute value so as to see how much the process under-estimates and/or over-estimates the IMT measure. The units of the calculated HD and PD are initially in pixels, but for our performance evaluation we converted the calculated pixel distances into millimeters, using a calibration factor, which is equal to the axial spatial resolution of the images. In our database, the 200 images acquired at the Neurology Division of Torino had a calibration factor equal to 0.0625 mm/pixel while the 100 images acquired at the Cyprus Institute of Neurology had a calibration factor equal to 0.0600 mm/pixel.

Third, for an overall assessment of the process performance, we calculated the Figure of Merit (FoM) which is defined by the following formula:

$$FoM = \left(1 - \frac{|IMT_{GT} - IMT_{CADLES-EF}|}{IMT_{CADLES-EF}}\right) \times 100 \quad (36)$$

FIG. 29A shows the LIMA borders with GT on two different kinds of geometries of Carotid Artery. FIG. 29B shows the nine samples randomly taken from the data of 300 images. Finally, the error values are shown in Table I and Table II. The Hausdorff distances between the GT and the computed $AD_F$ profiles are expressed in millimeters. The Polyline distance (eq. 35) between LI. (from edge flow method) and $LI_{GT}$ (ground truth) is expressed in mm. The fourth column reports the average estimated IMT by the techniques, the fifth the corresponding IMT measured by humans, and the sixth the FoM (computed using the above equation).

Table 1 shows the far adventitia ($AD_F$) error with respect to GT-LI and GT-MA.

TABLE 1

(LI AND MA RESULTS OF EDGE FLOW METHOD)
Overall performances of the EDGE FLOW algorithm compared with CALEXia and CULEXsa.

|  | GT LI-ADF error | GT MA-ADF error | LI-GT LI error | MA-GT MA error |
|---|---|---|---|---|
| Edge Flow | 2.327 ± 1.394 mm | 1.632 ± 1.584 mm | 0.475 ± 1.660 mm | 0.176 ± 0.202 mm |
| CALEXia | 2.733 ± 2.895 mm | 2.036 ± 3.024 mm | 0.406 ± 0.835 mm | 0.313 ± 0.850 mm |
| CULEXsa | 2.651 ± 1.436 mm | 1.965 ± 1.733 mm | 0.124 ± 0.142 mm | 0.118 ± 0.126 mm |

The image database consisted of 300 longitudinal images. The Hausdorff distances between the GT and the computed $AD_F$ profiles is expressed in millimeters. The Polyline distance been LI and $L_{GT}$ is expressed in mm.

Table 2 shoes IMT results.

TABLE 2

(IMT RESULTS OF EDGE FLOW METHOD)
More overall performances of the EDGE FLOW algorithm compared with CALEXia and CULEXsa.

|  | Number of images automatically processed | Number of images used for statistics | Estimated IMT | GT IMT | FoM |
|---|---|---|---|---|---|
| Edge Flow | 298 (99.3% of total) | 285 (95% of total) | 0.861 ± 0.276 mm | 0.818 ± 0.246 mm | 94.8% |
| CALEXia | 294 (98% of total) | 294 (98% of total) | 0.746 ± 0.156 mm | 0.880 ± 0.164 mm | 84.7% |
| CULEXsa | 286 (95.3% of total) | 275 (91.7% of total) | 0.805 ± 0.248 mm | 0.879 ± 0.237 mm | 91.5% |

The image database consisted of 300 longitudinal images. The fourth column reports the average estimated IMT by the techniques, the fifth the corresponding IMT measured by humans, and the sixth the FoM.

Figure 30:
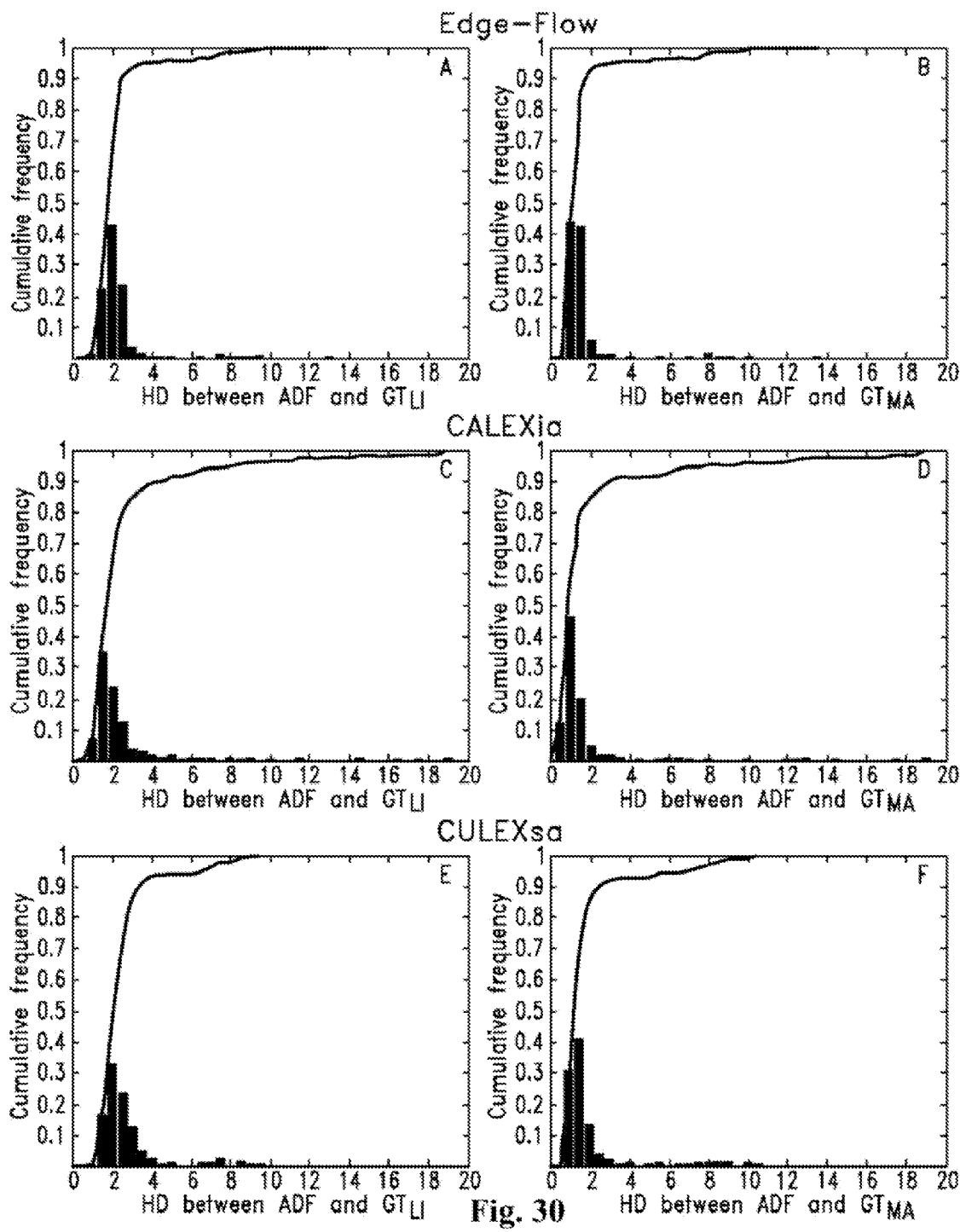
FIG. 30 shows the cumulative distribution.
Figure 31:
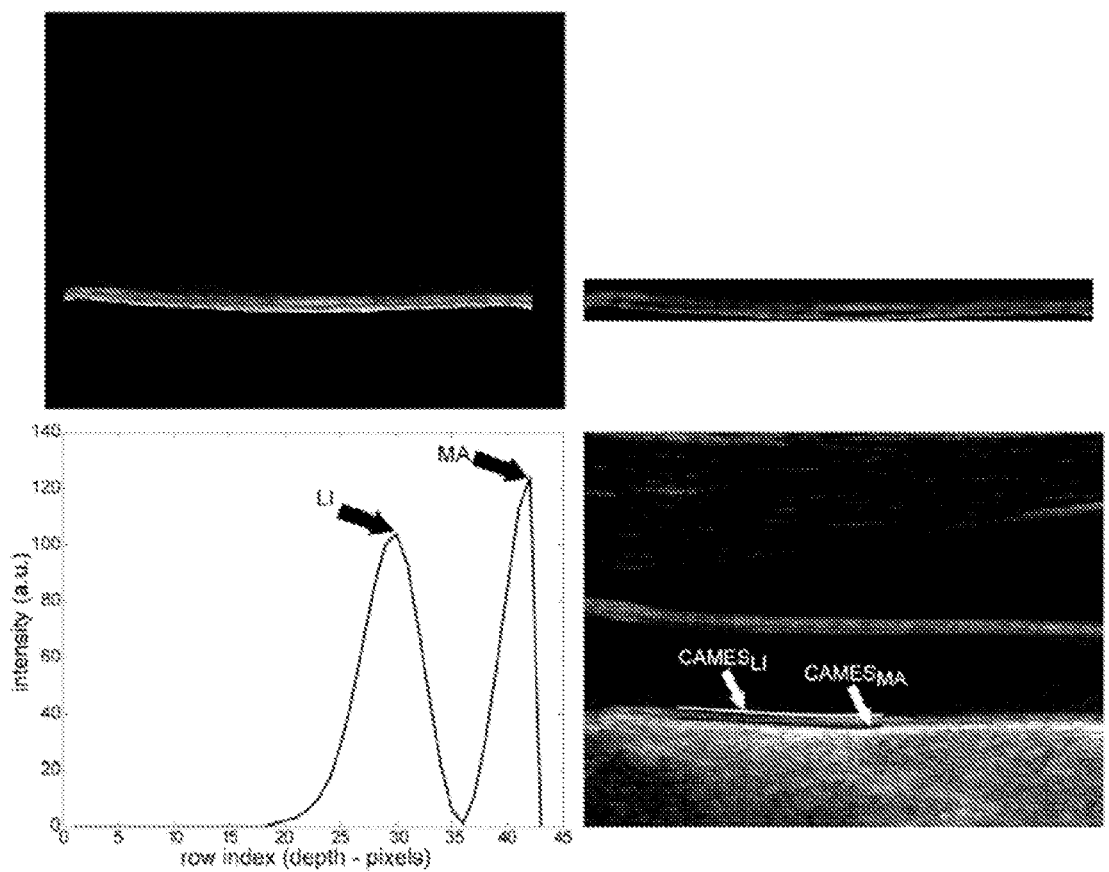
FIG. 31 shows the process for stage II (using moments).
Figure 32:
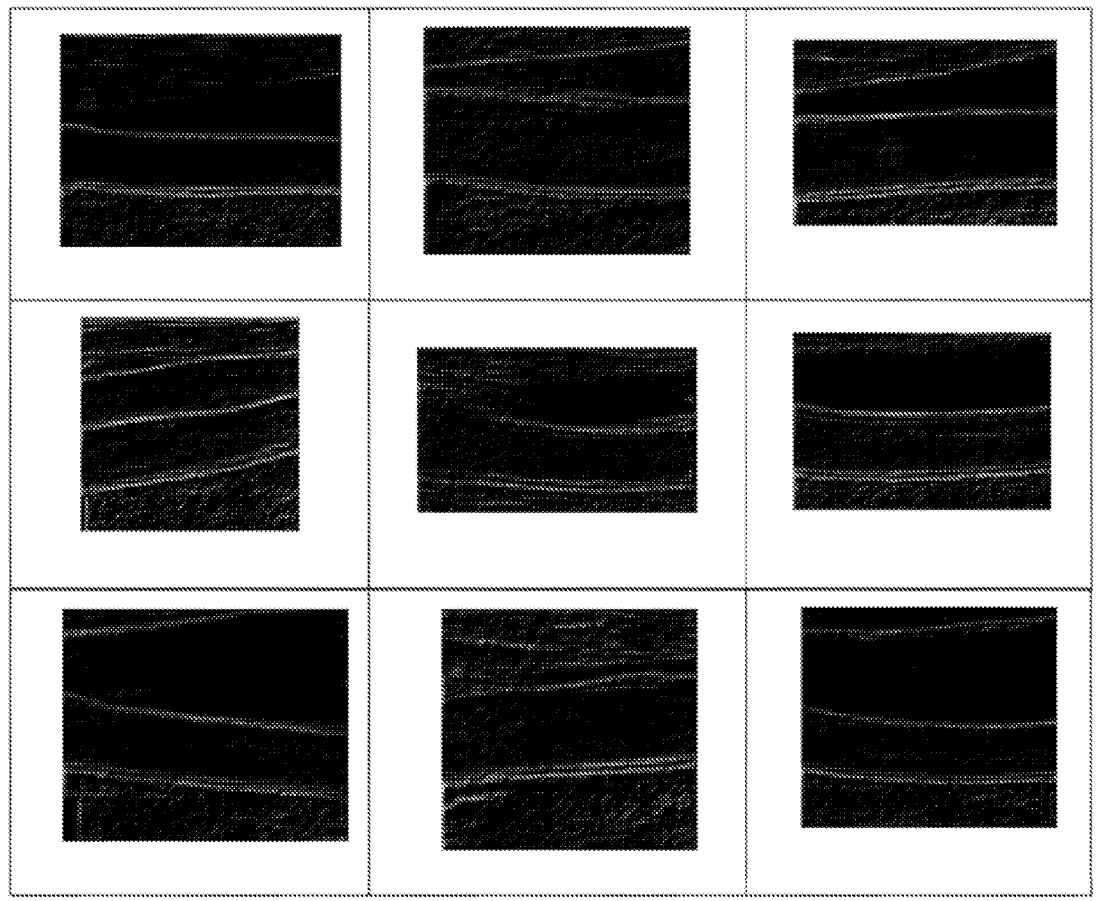
FIG. 32 shows the process for stage II (using CAMES).
Figure 33:
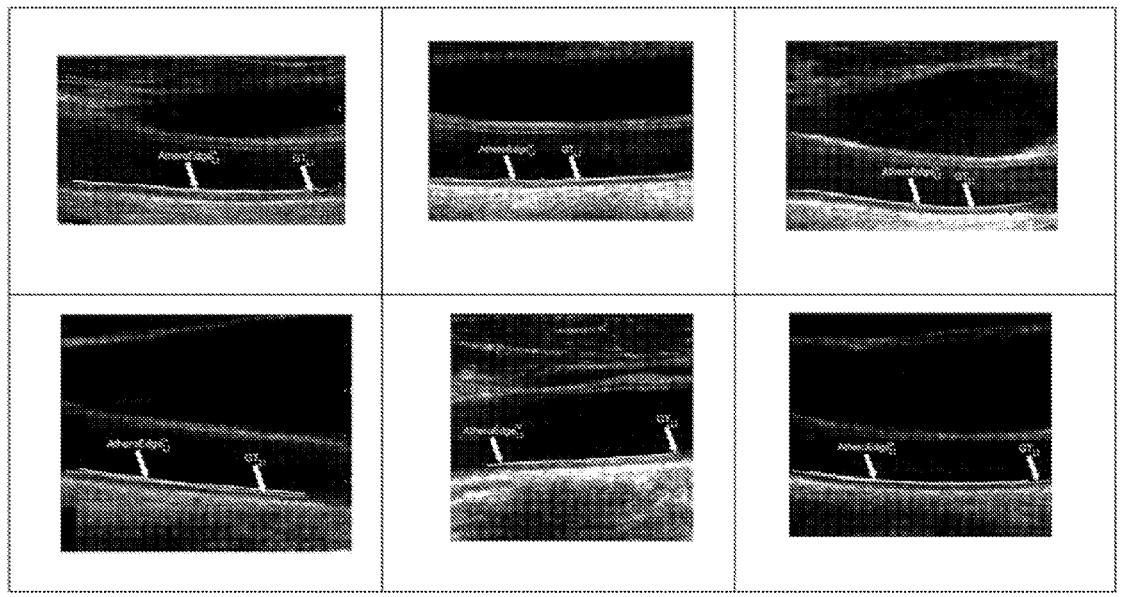
FIG. 33 shows the process for stage II (edge results).

FIG. 30 shows the distribution of the ADF error $\epsilon_{ADF-GT}^{LI}$ and MA error $\epsilon_{ADF-GT}^{MA}$ both with respect to the GT. FIG. 30 shows the Distribution of $\epsilon_{ADF-GT}^{LI}$ and $\epsilon_{ADF-GT}^{MA}$ for the EDGE FLOW method described herein relative to the results achieved for prior methods known as CALEXia, and CULEXsa. CALEXia, and CULEXsa are previous automated methods for processing ultrasound images. A description of the CULEXsa method can be found in the following document: "Characterization of a Completely User-Independent Algorithm for Carotid Artery Segmentation in 2-D Ultrasound Images", Silvia Delsanto et al., *IEEE Transactions On Instrumentation And Measurement*, Vol. 56, No. 4, August, 2007. A description of the CALEXia method can be found in the following document: "An Integrated Approach to Computer-Based Automated Tracing and Its Validation for 200 Common Carotid Arterial Wall Ultrasound Images, A New Technique", Filippo Molinari, et al., *Journal of Ultrasound in Medicine*, 2010, 29:399-418. Distribution of $\epsilon_{ADF-GT}^{LI}$ and $\epsilon_{ADF-GT}^{MA}$ for Edge Flow, CALEXia and CULEXsa, and LI and MA errors for Edge Flow are shown, respectively, in FIG. 30. FIG. 30 also shows the LI and MA errors for CALEXia, respectively. FIG. 30 also shows LI and MA errors for CULEXsa, respectively. The horizontal axis represents the error classes in millimeters and the vertical axis represents the cumulative frequency. The black lines represent the cumulative function of the error distributions. FIG. 31 shows the process for stage II (using moments). FIG. 32 shows the process for stage II using the process described in the priority application referenced above and denoted herein as CAMES. FIG. 33 shows the process for stage II (edge results).

Figure 34:
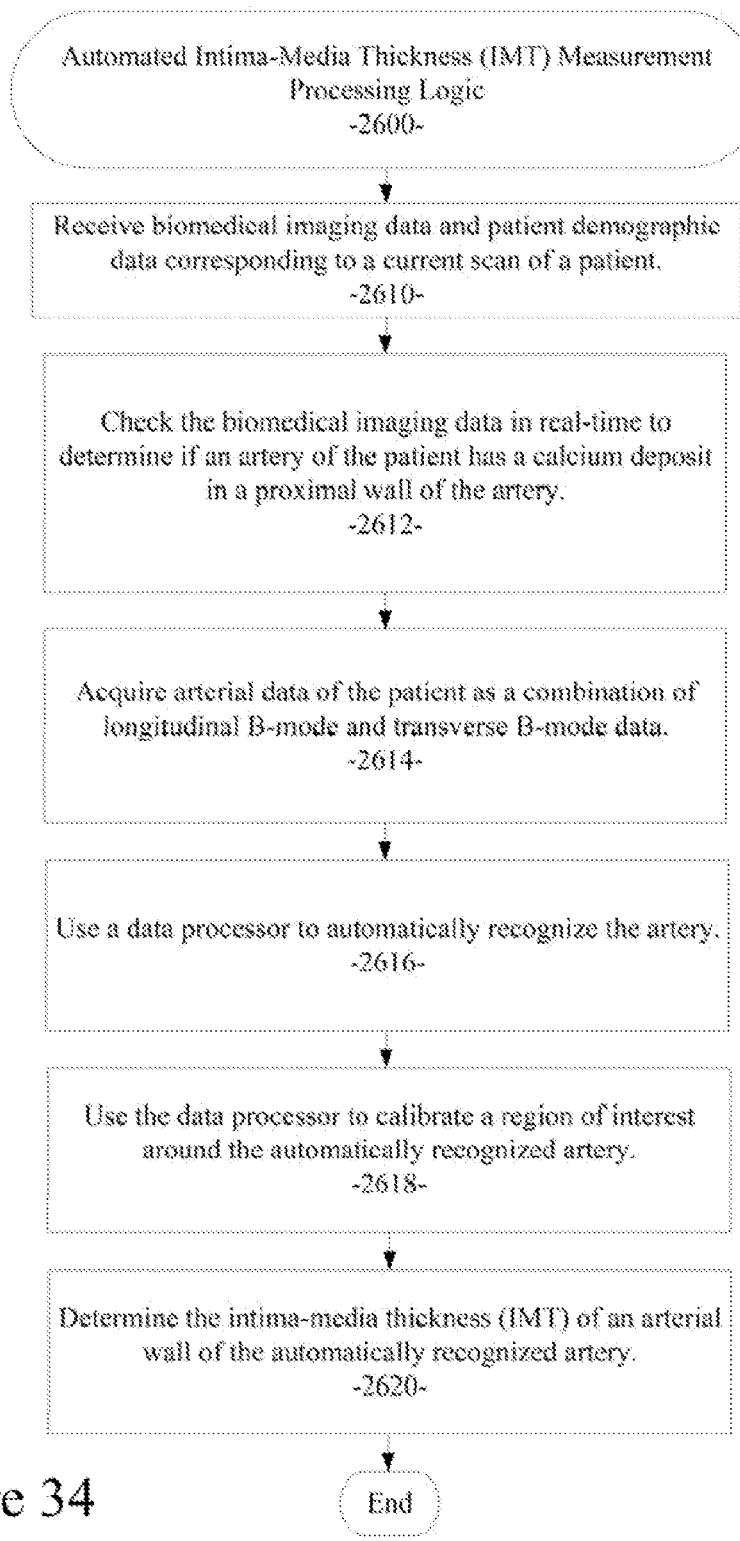
FIG. 34 is a processing flow diagram illustrating an example embodiment of a computer-implemented system and method for fast, reliable, and automated embodiments for using a multi-resolution edge flow approach to vascular ultrasound for intima-media thickness (IMT) measurement as described herein.

FIG. 34 is a processing flow diagram illustrating an example embodiment of a computer-implemented system and method for fast, reliable and automated processing for intima-media thickness (IMT) measurements as described herein. The method 2600 of an example embodiment includes: receiving biomedical imaging data and patient demographic data corresponding to a current scan of a patient (processing block 2610); checking the biomedical imaging data in real-time to determine if an artery of the patient has a calcium deposit in a proximal wall of the artery (processing block 2612); acquiring arterial data of the patient as a combination of longitudinal B-mode and transverse B-mode data (processing block 2614); using a data processor to automatically recognize the artery (processing block 2616); using the data processor to calibrate a region of interest around the automatically recognized artery (processing block 2618); and determining the intima-media thickness (IMT) of an arterial wall of the automatically recognized artery (processing block 2620).

Figure 35:
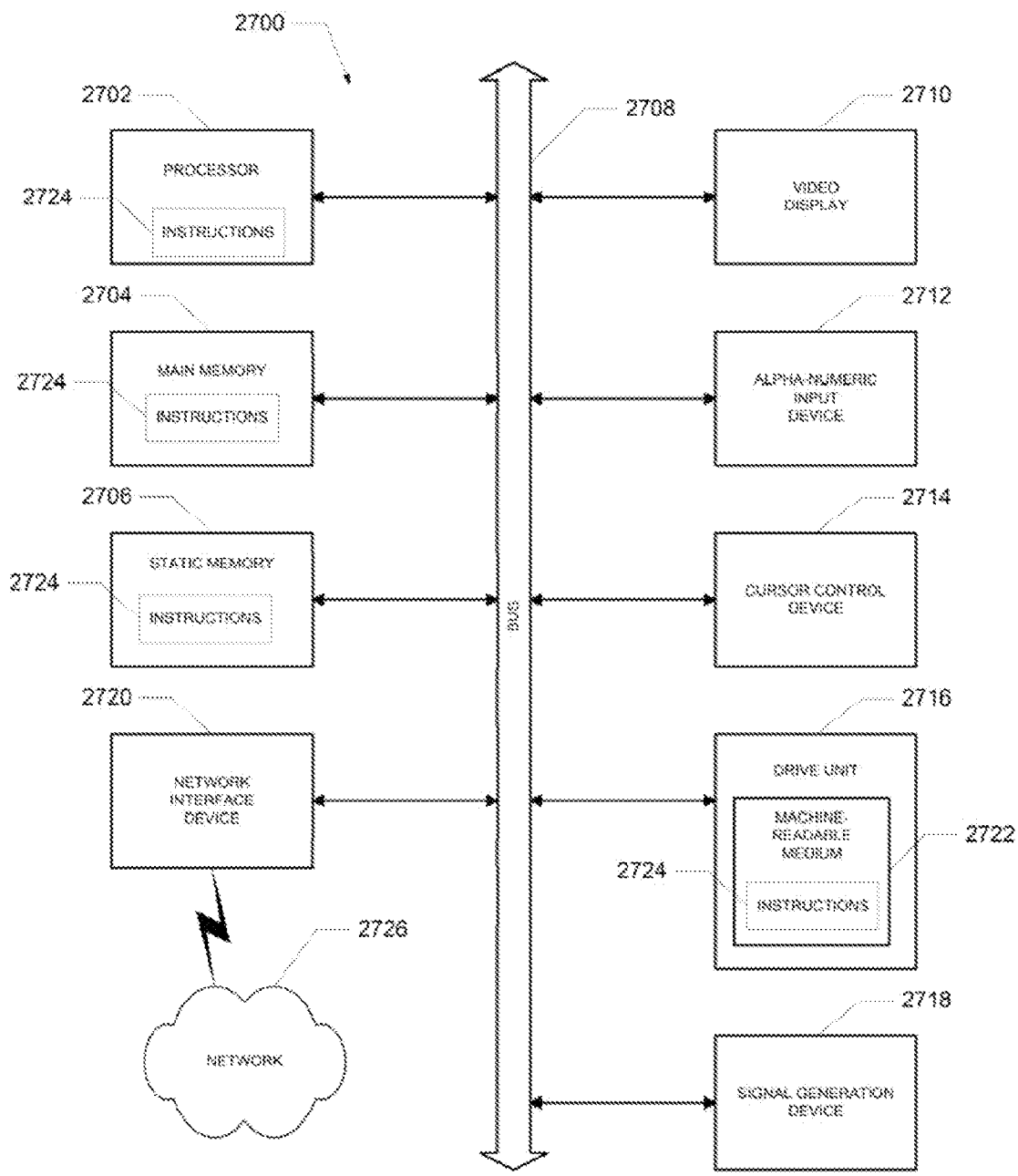
FIG. 35 shows a diagrammatic representation of machine in the example form of a computer system within which a set of instructions when executed may cause the machine to perform any one or more of the methodologies discussed herein.

FIG. 35 shows a diagrammatic representation of machine in the example form of a computer system 2700 within which a set of instructions when executed may cause the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" can also be taken to include any collection of machines that individually or jointly execute a set (or multiple sets) of instructions to perform any one or more of the methodologies discussed herein.

The example computer system 2700 includes a processor 2702 (e.g., a central processing unit (CPU), a graphics processing unit (GPU), or both), a main memory 2704 and a static memory 2706, which communicate with each other via a bus 2708. The computer system 2700 may further include a video display unit 2710 (e.g., a liquid crystal display (LCD) or a cathode ray tube (CRT)). The computer system 2700 also includes an input device 2712 (e.g., a keyboard), a cursor control device 2714 (e.g., a mouse), a disk drive unit 2716, a signal generation device 2718 (e.g., a speaker) and a network interface device 2720.

The disk drive unit 2716 includes a machine-readable medium 2722 on which is stored one or more sets of instructions (e.g., software 2724) embodying any one or more of the methodologies or functions described herein. The instructions 2724 may also reside, completely or at least partially, within the main memory 2704, the static memory 2706, and/or within the processor 2702 during execution thereof by the computer system 2700. The main memory 2704 and the processor 2702 also may constitute machine-readable media. The instructions 2724 may further be transmitted or received over a network 2726 via the network interface device 2720. While the machine-readable medium 2722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A computer-implemented method to correct shadow regions in a current scan of a patient; the method comprising:
    receiving biomedical imaging data and patient demographic, data corresponding to the current scan of a patient;
    checking the biomedical imaging data in real-time to determine if an artery of the patient has a calcium deposit in a proximal wall of the artery;
    acquiring arterial data of the patient as a combination of longitudinal B-mode and transverse B-mode data;
    using a data processor to automatically recognize the artery in a distal wall;
    using the data processor to calibrate a region of interest around the automatically recognized artery using edge flow, the region of interest being automatically calibrated;
    determining, automatically, the intima-media thickness (IMT) of an arterial wall of the automatically recognized artery; and
    using the data processor to correct the IMT in the shadow regions in longitudinal B-mode ultrasound images by use of information from transverse B-mode ultrasound images.

2. The method as claimed in claim 1 wherein the method is applied to calcium and non-calcium arterial IMT measurement.

3. The method as claimed in claim 1 wherein the method is applied for automated recognition using a process including one or more from the group: a) a multi-resolution approach, b) a multi-resolution approach, where borders of the arterial wall are determined in coarse resolution, or c) a multi-resolution approach, where borders of the arterial wall are determined in coarse resolution and up-sampled back onto the original high resolution image.

4. The method as claimed in claim 1 including reducing speckle in real time in the region where the automated artery is recognized.

5. The method as claimed in claim 1 including computing a coarse resolution by convolution of higher order derivative of Gaussian kernels.

6. The method as claimed in claim 1 including computing a coarse resolution by convolution of higher order derivative of Gaussian kernels with and without calcium present in the arterial proximal wall.

7. The method as claimed in claim 1 wherein the automated recognition is implemented using a feature based method.

8. The method as claimed in claim 1 wherein the calibration of the region is guided by an edge flow method.

9. The method as claimed in claim 1 wherein the calibration of the region includes computing edge energy based on intensity and texture.

10. The method as claimed in claim 1 including computing a lumen-intima (LI) calibration based on media-adventitia (MA) using a dependency approach using connectivity and labelling.

11. The method as claimed in claim 1 including computing a media-adventitia (MA) and lumen-intima (LI) calibration from a border of the arterial wall calculation.

12. The method as claimed in claim 1 including computing weak or missing media-adventitia (MA) edges from strong MA edges.

13. The method as claimed in claim 1 including computing weak or missing lumen-intima (LI) edges from strong LI edges and full media-adventitia (MA) edges.

14. The method as claimed in claim 1 including monitoring the IMT for patients which are under clinical trials.

15. The method as claimed in claim 1 including computing the IMT of a batch of patients in clinical databases automatically.

16. The method as claimed in claim 1 including computing the IMT using knowledge of ethnicity, demographics, age, and gender of patients.

17. The method as claimed in claim 1 including changing a calibration by a classifier, by a deformable model, by an edge detector, or by a combination of an edge detector with deformable model.

* * * * *